(12) United States Patent
Brehm et al.

(10) Patent No.: US 7,355,027 B2
(45) Date of Patent: Apr. 8, 2008

(54) BACILLUS ANTHRACIS PROTECTIVE ANTIGEN

(75) Inventors: John Brehm, Salisbury (GB); Ian McEntee, Salisbury (GB); Philip Vincent, Salisbury (GB); Nigel Allison, Salisbury (GB); Rossalyn Brehm, Salisbury (GB); George Jack, Salisbury (GB); Michael Herbert, Salisbury (GB); Barbara T. Solow, Frederick, MD (US); Juan Arroyo, Frederick, MD (US); Randall K. Lapcevich, Frederick, MD (US)

(73) Assignees: Dynport Vaccine Company LLC, Frederick, MD (US); Health Protection Agency, Salisbury, Wiltshire (GB)

( * ) Notice: Subject to any disclaimer, the term of this patent is extended or adjusted under 35 U.S.C. 154(b) by 0 days.

(21) Appl. No.: 11/153,865

(22) Filed: Jun. 15, 2005

(65) Prior Publication Data

US 2008/0020001 A1    Jan. 24, 2008

Related U.S. Application Data

(60) Provisional application No. 60/579,687, filed on Jun. 16, 2004.

(30) Foreign Application Priority Data

Jun. 16, 2004    (GB) .................................. 0413475.5

(51) Int. Cl.
C07H 21/04    (2006.01)
(52) U.S. Cl. .................................. 536/23.7; 435/320.1
(58) Field of Classification Search ...................... None
See application file for complete search history.

(56) References Cited

U.S. PATENT DOCUMENTS 5,670,333 A * 9/1997 Alldread et al. ........... 435/69.1
2004/0028695 A1    2/2004 Park

FOREIGN PATENT DOCUMENTS

| EP | 0121352 A1 * | 10/1984 |
|---|---|---|
| WO | WO 98/08952 | 3/1998 |
| WO | WO 02/04646 | 1/2002 |
| WO | WO 03/040179 | 5/2003 |
| WO | WO 2004/003139 | 1/2004 |
| WO | WO 2004/024067 | 3/2004 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Sigmund, Arterioscler. Thromb. Vasc. Biol., 20:1425-1429, 2000.*
Bampton et al., Brain Res., 841:123-134, 1999.*
Invitrogen Product Catalog, 2001.*
Novagen Catalog, 2002-2003.*
Colman, Res. Immunol., 145:33-36, 1994.*
Lewin, Genes IV, Oxford Univ. Press, 1990, p. 68.*
By Manju Sharma et al, "Expression and Purification of Anthrax Toxin Protective Antigen from *Escherichia coli*", Protein Expression and Purification, vol. 7, Article No. 0005, 1996, pp. 33-38.
Minton et al., The Complete Nucleotide Sequence of the *Pseudomonas* Gene Coding For Carboxypeptidase G2, Gene, 31 (1984) 31-38, XP002038770.
Ascenzi et al., Anthrax Toxin: A Tripartite Lethal Combination, FEBS Letters 531 (2002) 384-388.

* cited by examiner

*Primary Examiner*—Robert A. Zeman
*Assistant Examiner*—Brian Gangle
(74) *Attorney, Agent, or Firm*—Foley Hoag LLP

(57) ABSTRACT

A polynucleotide sequence is provided, comprising: a nucleic acid sequence having at least 75% identity to SEQ ID NO: 1, wherein said nucleic acid sequence encodes recombinant *Bacillus anthracis* Protective Antigen (rPA); or a fragment of said nucleic acid sequence wherein said fragment encodes a fragment of recombinant *Bacillus anthracis* Protective Antigen (rPA).

Also provided are expression vectors and host cells comprising the polynucleotide sequence of the invention, and methods for producing rPA or a fragment thereof.

The invention further provides antigenic compositions and corresponding methods and uses for inducing an immune response.

23 Claims, 23 Drawing Sheets

10h  12h  14h  16h  18h  20h  22h  24h  -ve  Stds

Stds  10h  12h  14h  16h  18h  20h  22h  24h  -ve

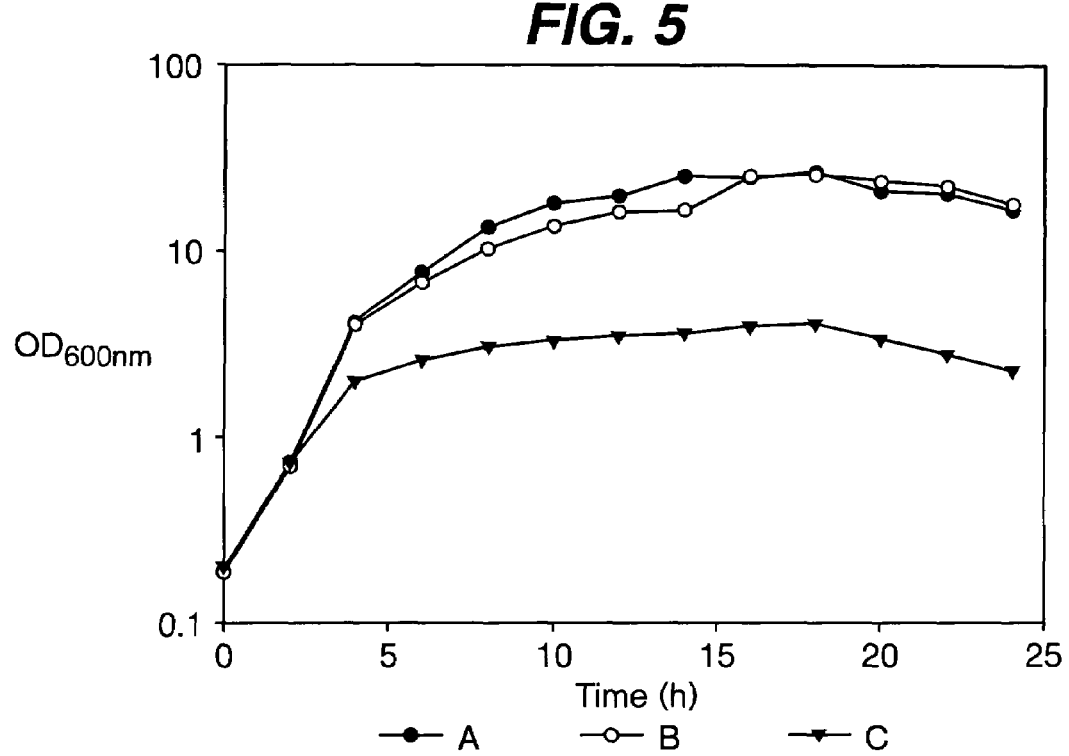

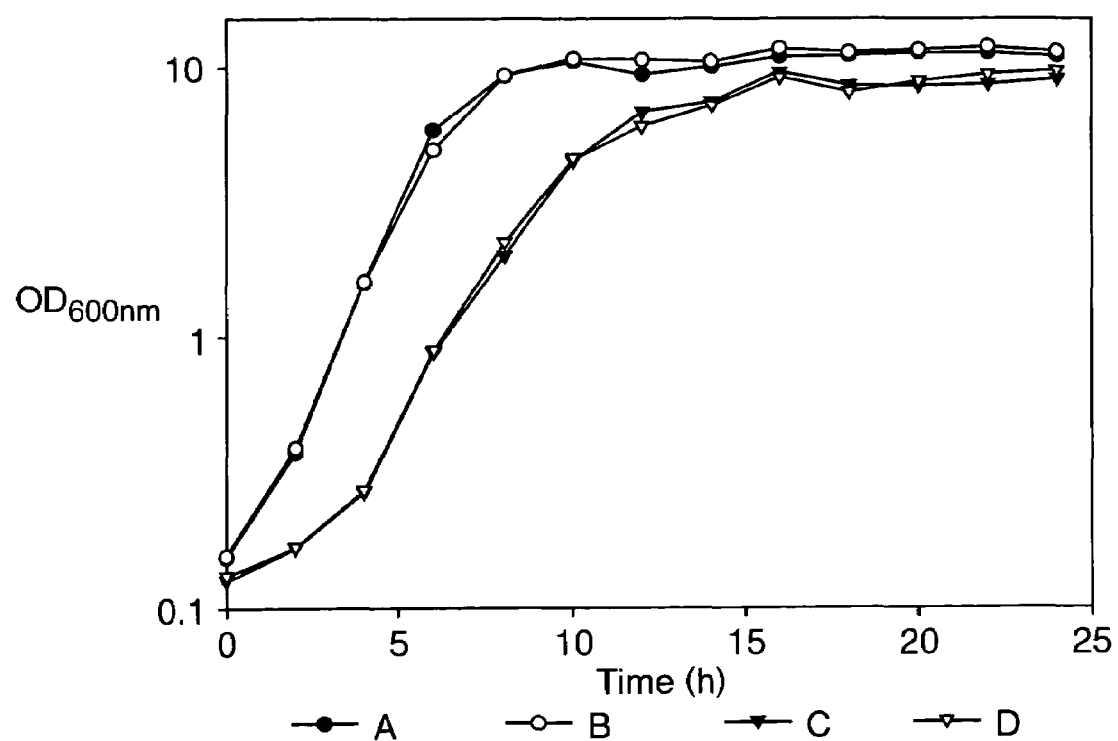

FIG 13(A1)

ATGGAAGTTAAACAGGAGAACCGTTTGTTGAATGAATGCGAATCTAGTTCTCAGGGGTTGCTGGGCTACT 10 20 30 40 50 60 70

DVC.Synthetic.rP ATGGAAGTGAAACAGGAGAACCGTCTGCTGAACGAAAGCGAATCTAGCTCTCAGGGCCTGCTGGGCTACT 70
AP.PA.wt.Sequenc ATGGAAGTTAAACAGGAGAACCGGTTATTAAATGAATCAGAATCAAGTTCCCAGGGGTTACTAGGATACT 70

ATTTTAGTGATTTGAATTTTCAGGCACCGATGGTTGTTACCTCTTGTACTACCGGGGATTTGTGTATTCC 80 90 100 110 120 130 140

DVC.Synthetic.rP ATTTCAGCGATCTGAACTTTCAGGCACCGATGGTTGTGACCTCTAGCACGACCGGCGATCTGAGCATTCC 140
AP.PA.wt.Sequenc ATTTTAGTGATTTGAATTTTCAAGCACCCATGGTGGTTACCTCTTCTACTACAGGGGATTTATCTATTCC 140

TAGTTGTGAGTTGGAGAATATTCCGTGGGAGAACCAGTATTTTCAGTCTGCTATTTGGTGCGGCTTTATC 150 160 170 180 190 200 210

DVC.Synthetic.rP GAGCAGCGAACTGGAGAACATTCCGAGCGAGAACCAGTACTTTCAGTCTGCGATTTGGAGCGGCTTCATC 210
AP.PA.wt.Sequenc TAGTTCTGAGTTAGAAAATATTCCATCGGAAAACCAATATTTTCAATCTGCTATTTGGTCAGGATTTATC 210

FIG 13(A2)

```
                      AAAGTTAAGAAGAGTGATGAGTATACCTTTGCTACTTCTGCTGATAATCATGTGACCATGTGGGTGGATG
                      |----------|----------|----------|----------|----------|----------|
                     220        230        240        250        260        270        280

DVC.Synthetic.rP  AAAGTGAAGAAAAGCGATGAGTATACCTTTGCGACGTCTGCCGGATAACCATGTGACCATGTGGGTGGACG  280
AP.PA.wt.Sequenc  AAAGTTAAGAAGAGTGATGAATATACACATTGCTACTTCCGCTGATAATCATGTAACAATGTGGGTAGATG  280

ATCAGGAAGTGATTAATAAAGCTTGTAATTGTAACAAGATTCGCTTGGAGAAGGGTCGCTTGTTGTATCAGAT
                      |----------|----------|----------|----------|----------|----------|
                     290        300        310        320        330        340        350

DVC.Synthetic.rP  ATCAGGAAGTGATCAACAAAGCGAGCAACAAGATTCGCCTGGAGAAGGGTCGCCTGTATCAGAT  350
AP.PA.wt.Sequenc  ACCAAGAAGTGATTAATAAAGCTTCTAATTCTAACAAAATCAGATTAGAAAAGGAAGATTATATCAAAT  350

CAAGATTCAGTATCAGCGCGAGAATCCTACTGAGAAGGCTTGGAATTTCAAGTTGTACTGGACCGATTGT
                      |----------|----------|----------|----------|----------|----------|
                     360        370        380        390        400        410        420

DVC.Synthetic.rP  CAAGATTCAGTATCAGCGCGAGAATCCGACCGAGAATCCGGATTTCAAACTGTACTGGACCGATAGC  420
AP.PA.wt.Sequenc  AAAAATTCAATATCAACGAGAGAAAATCCTACTGAAAAAAGGATTGGATTTCAAGTTGTACTGGACCGATTCT  420
```

FIG 13(A3)

```
                              CAGAATAAGAAGAAGTGATTGTTGTGATAACTTGCAATTGCCGGAATTGAAACAGAAGTGTTGAACT
                              |        |        |        |        |        |        |
                              430      440      450      460      470      480      490
DVC.Synthetic.rP  CAGAACAAGAAGAAGTGATTAGCTCTGATAACCTGCAACTGAAACAGAAGAGCAGCAACA 490
AP.PA.wt.Sequenc  CAAAATAAAAAAGAAGTGATTTCTAGTGATAACTTACAATTGCCAGAATTAAAACAAAATCTTGAACT 490

GCCCGCAAGAAGCGCAGTACCTGTGCTGGCCCCTACGGTTCCAGATCGTGACAATGATGGCATTCCTGATTG
                              |        |        |        |        |        |        |
                              500      510      520      530      540      550      560
DVC.Synthetic.rP  GCCCGCAAGAAACGCAGCACCTCTGCAGGCCCGACCTGCGACAACGATGGCATTCCGGACAG 560
AP.PA.wt.Sequenc  CAAGAAAAAAGCGAGTACAAGTGCTGGACCTACGGTTCCAGACCGTGACAATGATGAATCCCTGATTC 560

CTTGGAGGTGGAAGGTTATACGGTTGATGTGAAGAATAAACGCACTTTTCTTTGCCCGTGGATTGTAAT
                              |        |        |        |        |        |        |
                              570      580      590      600      610      620      630
DVC.Synthetic.rP  CCTGGAAGTGGAAGGTTATACCGTTGATGTGAAGAACAAACGCACCTTTCTGAGCCCGTGATTAGCAAC 630
AP.PA.wt.Sequenc  ATTAGAGTAGAAGGATATACGGTTGATGTCAAAAATAAAGAACTTTCTTTCACCATGGATTTCTAAT 630
```

FIG 13(B1)

```
                       ATTCATGAGAAGAAAGGCTTGACCAAGTATAAATGCTGTCCTGAGAAGTGGAGCACGGCTTGTGATCCGT
                       |      |      |      |      |      |      |
                      640    650    660    670    680    690    700

DVC.Synthetic.rP ATTCATGAGAAGAAAGGCTTGACCAAGTATAAATGCTGTCCTGAGAAGTGGAGCACGGCTTGTGATCCGT  700
AP.PA.wt.Sequenc ATTCATGAAAAGAAAGGATTAACCAAATATAAATCATCTCCTGAAAAATGAGCACGGCTTCTGATCCGT  700

ATAGTGATTTTGAGAAGTTACCGGCCGGATTGATAAGAATGTGTGCCCGAGGCGCGTCACCCCCTTGT
                       |      |      |      |      |      |      |
                      710    720    730    740    750    760    770

DVC.Synthetic.rP ATAGCGACTTTGAGAAGTTACCGGCCGCATTGATAAGAACGTGAGCCCGGAAGCGCGTCACCCACTGGT  770
AP.PA.wt.Sequenc ACAGTGATTTGCAAAAGTTACAGGACGGATTGATAAGAATGTATCACCAGAGCAAGACACCCCCTTGT  770

TGCAGCTTATCCGATTGTGCATGTTGATGTTGCATGTTGACATGGAGAACATCATTCTGAGCAAGAACGAAGATCAGAGCACC
                       |      |      |      |      |      |      |
                      780    790    800    810    820    830    840

DVC.Synthetic.rP TGCAGCGTTATCCGATTGTGCATGTTGACATGTTGACATGGAGAACATCATTCTGAGCAAGAACGAAGATCAGAGCACC  840
AP.PA.wt.Sequenc GGCAGCTTATCCGATTGTGCATGTTGTACATGTAGATATGTGAGAATATTATTCTCTCAAAAAATGAGGATCAATCCACA  840
```

FIG 13(B2)

```
DVC.Synthetic.rP  CAGAATACTGATAGTCAGACGCGCACGATCAGTAAGAATACTTGTACGAGTCGTACCCATACTAGTGAAG  910
AP.PA.wt.Sequenc  CAGAATACTGATAGTCAGACCCGCACGATCAGCAAGAACACCAGCACGAGCCGTACCATACCAGCGAAG  910
                      850       860       870       880       890       900       910

DVC.Synthetic.rP  TGCATGGCAATGCGGAAGTGCATGCGGAGCTTCTTTGACATTGGTGTGCAGCGTGAGCGCGGGCTTCAGCAA  980
AP.PA.wt.Sequenc  TACATGAAATGCAGAAGTGCATGCGTCGTTCTTGATATTGGTGGGAGTGTATCTGCAGGATTAGTAA  980
                      920       930       940       950       960       970       980

DVC.Synthetic.rP  TTGGAATTGCAGTACGGTTGGCGATTGATCATTGCCTGTCTGCGGGGGAACGTACTTGGGCTGAAACC  1050
AP.PA.wt.Sequenc  TTCGAATTCAAGTACGTCGCAATTGATCATTCACTATCTCTAGCAGGGAAAGAACTTGGGCTGAAACA  1050
                      990       1000      1010      1020      1030      1040      1050
```

FIG 13(B3)

```
                      ATGGGTTTGAATACGGCTGATACGGCACGTTTGAATGCGAATATTCGCTATGTGAATACTGGTACGGCTC
DVC.Synthetic.rP      ATGGGCCTGAACACGGCGGATACGGGCACGTCTGAATGCGAACATTCGCTATGTGAACACCGGTACCGCGC    1120
AP.PA.wt.Sequenc      ATGGGTTTAAATACCGCTGATACAGCAAGAGATTAAATGCCAATATTAGATATGTAAATACTGGGACGGCTC    1120
                      |----|----|----|----|----|----|----|----|----|----|----|----|----|
                        1060     1070     1080     1090     1100     1110     1120

CAATCTATAACGTTTGCCGACGTTGGTGTTGGGCAAGAATCAGACCCTGGCGACCATTAAAGC
DVC.Synthetic.rP      CAATCTATAACGTTCTGCCGACCACGAGCCTGGTGCTGGGCAAGAATCAGACCCTGGCGACCATCAAAGC    1190
AP.PA.wt.Sequenc      CAATCTACAACGTGTTACCAACGACTTCGTTAGTGTTAGGAAAAATCAAACACTCGACAATTAAAGC    1190
                      |----|----|----|----|----|----|----|----|----|----|----|----|
                        1130     1140     1150     1160     1170     1180     1190

TAAGGAGAACCAGTGTGTCAGATTCTTGCACCTAATAATTATTATCCTTGTAAGAACTTGGCGCCGATT
DVC.Synthetic.rP      GAAAGAGAACCAGCTGTCTCAGATTCTGGCACCGAACAACTACTATCCGAGCAAGAACTTGGCACCGATT    1260
AP.PA.wt.Sequenc      TAAGGAAAAACCAATTAAGTCAAATACTTGCACCTAATAATTATTATCCTTCTAAAAAACTTGGCGCCAATC    1260
                      |----|----|----|----|----|----|----|----|----|----|----|----|
                        1200     1210     1220     1230     1240     1250     1260
```

FIG. 13(C1)

```
                          GCATTGAATGCGCAGGATGATTTCAGTTGTACTCCGATTGTGTACCATGAATTACAATCAGTTTCTTGAGTTGG
                          ├────┬────┼────┬────┼────┬────┼────┬────┼────┬────┼────┬────┼────┬────┤
                          1270      1280      1290      1300      1310      1320      1330

DVC.Synthetic.rP  GCACTGAATGCGCAGGATGACTTCAGCAGCACCCCGATCACCATGAACTACAATCAGTTTCTGGAGCTGG  1330
AP.PA.wt.Sequenc  GCATTAAATGCACAAGACGATTTCAGTTCTACTCCAATTACAATGAATTACAATCAATTTCTTGAGTTAG  1330

AGAAGACGAAACAATTGCGCTTGGATACGGATCAGTGTATGGGAATATTGCGACCTACAATTTTGAGAAA
                          ├────┬────┼────┬────┼────┬────┼────┬────┼────┬────┼────┬────┼────┬────┤
                          1340      1350      1360      1370      1380      1390      1400

DVC.Synthetic.rP  AGAAGACCAAACAACAACTGCGCCTGGATACCGATCAGGTGTATGGCAACATTGCGACCTACAACTTTGAGAA  1400
AP.PA.wt.Sequenc  AAAAAACGAAACAATTAAGATTAGATACGGATCAAGTATACGAATATAGCAACATACAATTTTGAAAA    1400

TGGCCGCGTTCGGGTTGGATACCGGTTGGAACTGGTGTGTTGCCGCAGATTCAGGAAACGACTGCG
                          ├────┬────┼────┬────┼────┬────┼────┬────┼────┬────┼────┬────┼────┬────┤
                          1410      1420      1430      1440      1450      1460      1470

DVC.Synthetic.rP  CGGCCGCGTTCGCGTTCCGCGTTGGATACCGGTCGATACCGGTAGCAACTGGTCTGAAGTGCTGCCGCAGATTCAGGAAACGACCGCG  1470
AP.PA.wt.Sequenc  TGGAAGAGTGAGGGTGATACAGGCTGAAGTGTTACCGCCGAAGTGTTACCGGAGTGAAGTGAAACAACTGCA  1470
```

FIG. 13(C2)

```
                         1480       1490       1500       1510       1520       1530       1540
DVC.Synthetic.rP CGCATCATCTTCAACGGCAAAGATCTGAACCTGGTGAACGTCGCATCGCGGCAGTGAACCCATCTGATC 1540
AP.PA.wt.Sequenc CGTATCATTTTTAATGAAAAGATTTAAATCTGGTAGAAAGGCGGATAGCGCGGTTAATCCTAGTGATC 1540
                         1550       1560       1570       1580       1590       1600       1610
DVC.Synthetic.rP CACTGGAAACGACCAAACCGGACCCTGAAAGAAGCGCTGAAGATTGCATTGGCTTCAACGAACC 1610
AP.PA.wt.Sequenc CATTAGAAACGACTAAACGGATATGACATTAAAAGAAGCCCTAAAATAGCATTGGATTAACGAACC 1610
                         1620       1630       1640       1650       1660       1670       1680
DVC.Synthetic.rP GAATGGCAACTTGCAGTATCAGGGCAAAGACATCACCGAGTTTGACTTCAACTTTGATCAACAGACCTCT 1680
AP.PA.wt.Sequenc GAATGGAAACTTACAATATCAAGGAAAGACATAACCGAATTTGATTTAATTTGATCAACAAACATCT 1680
```

FIG. 13(C3)

```
                 CAGAATATCAAGAATCAGTTGGCGGAATTGAATGCGACTAACATCTATACTGTGTTGGATAAGATCAAAT
DVC.Synthetic.rP CAGAAACATCAAGAACCAGCTGGCCAGAACTGAATGCGACCAACATCTACACCGTGCTGGACAAGATCAAAC 1750
AP.PA.wt.Sequenc CAAAATATCAAGAATCAGTTAGCGGAATTAAACGCAACTAACATATATACTGTATTAGATAAAATCAAAT   1750
                          1690      1700      1710      1720      1730      1740      1750

TGAATGCAAAGATGAATATTTGATTCGTGATAAACGTTTTCATTATGATCGTAATAACATTGCGGTTGG
DVC.Synthetic.rP TGAACGCAAAGATGAACATTCTGATTCGTGACAACGCTTCCACTATGATCGTAACAACATTGCGGTGGG   1820
AP.PA.wt.Sequenc TAAATGCAAAAATGAATATTTTAATAAGAGATAAACGTTTTCATTATGATAGAAATAACATAGCAGTTGG   1820
                          1760      1770      1780      1790      1800      1810      1820

TGCGGGATGAGTGCGTTGTTGTTAAGGAGGCTCATCGTGAAGTGATTAATTCTTGCACCGAGGGCTTGTGTTG
DVC.Synthetic.rP TGCAGAGATGAAAGCGTTGTGAAAGAAGCGCATCGTGAAGTGATCAACTCTAGCACCGAAGGCCTGCTGCTG 1890
AP.PA.wt.Sequenc GGCGGATGAGTCAGTAGTTAAGGAGTTAAGGAGGCTCATAGAGAAGTAATTAATTCGTCAACAGAGGGATTATTGTTA   1890
                          1830      1840      1850      1860      1870      1880      1890
```

FIG. 13(D2)

```
                 GCTGTTACTAAAAGAGAACACTATTATTAATCCTAGTGAGAATGGGGATACTAGTACCAACGGGATCAAGA
                 |       |       |       |       |       |       |
                 2110    2120    2130    2140    2150    2160    2170

DVC.Synthetic.rP GCGGTGACCAAAGAGAACACCATCATTAACCCAAGCGAGAATGGCGATACCAGCACCAACGGCATCAAGA 2170
AP.PA.wt.Sequenc GCTGTTACTAAAAGAGAACACTATTATTAATCCTAGTGAGAATGGGGATACTAGTACCAACGGGATCAAGA 2170

AGATTTTGATCTTTTGTAAGAAAGGCTATGAGATTGGCTAA
                 |       |       |       |
                 2180    2190    2200    2210

DVC.Synthetic.rP AGATTCTGATCTTCAGCAAGAAAGGCTATGAGATTGGCTAA                              2211
AP.PA.wt.Sequenc AAATTTTAATCTTTTCTAAAAAAGGCTATGAGATAGGATAA                              2211
```

BACILLUS ANTHRACIS PROTECTIVE ANTIGEN

CROSS-REFERENCE TO RELATED APPLICATION

This application claims the benefit of U.S. Provisional Patent Application Ser. No. 60/579,687 and GB Patent Application Serial No. 0413475.5, which were both filed on Jun. 16, 2004, and are hereby incorporated by reference.

FIELD OF THE INVENTION

The present invention relates to polynucleotides and vectors encoding recombinant *Bacillus anthracis* protective antigen (rPA), methods of producing rPA, and uses thereof in antigenic compositions, such as vaccines.

DESCRIPTION OF PREFERRED EMBODIMENTS

*Bacillus anthracis* is a Gram positive, spore-forming bacterium and the causative agent of anthrax. Anthrax is a disease of domestic and land animals, and can affect humans through contact with infected animal products. In the lungs, anthrax can cause massive fluid build-up, tissue decay, toxic shock and death.

Anthrax vaccine has been manufactured by the present Applicant for over 40 years and, since 1979, has been the subject of a UK Product Licence (PL1511/0037) held by the Secretary of State for Health. However, within that time there has been little product development or advance in its manufacturing process.

The above vaccine preparation is now described in more detail. Cultures of the toxigenic, non-capsulating *B. anthracis* 34F2 "Sterne" strain [see Sterne, M. (1939). Onderstepoort J. of Veterinary Science and Animal Industry, 13, pp 307-312] are grown in multiple 500 mL volumes in a partially defined medium in Thompson bottles at 37° C. until the pH of selected culture bottles falls below pH 7.4.

At the end of the growth period (approximately 24-28 hours) the cultures are harvested by aspiration, and the pooled supernatant fluids sterilised by filtration. Potassium aluminium sulphate solution is added, and the resulting solution mixed. The pH is then adjusted to 5.8-6.2, and the resulting flocculant ('alum-precipitation') allowed to settle under gravity for up to one week at 5° C.

The precipitate is then concentrated 20-fold (by volume) by aspiration, and diluted 1:4 with a saline solution to provide a '5-fold' concentrate of anthrax vaccine precipitate (AVP). This is the antigenic composition that is used for vaccine formulation. Although the vaccine is subjected to animal tests for potency and safety prior to human use, there is no separate routine biochemical characterisation.

One further cell-free anthrax vaccine is available for human use. This vaccine is produced in the United States of America and is broadly similar to that available under PL1511/0037, except that a different *B. anthracis* strain is used and grown anaerobically. The process is fermenter-based, and the culture filtrate is absorbed on to an aluminium hydroxide suspension.

Other available vaccines comprise live, attenuated spore suspensions. However, because of the inherent risks associated with attenuated pathogens, these vaccines are usually restricted to non-human use.

Anthrax toxin consists of three distinct polypeptides known as protective antigen (PA), oedema factor (EF), and lethal factor (LF). The toxin components act in specific binary combinations of PA and EF to form oedema toxin (ET), which causes tissue oedema, and of PA and LF to form lethal toxin (LT), which is lethal to laboratory animals and causes lysis of monocyte and macrophage cells. Lethal toxin is considered to be the principal cause of anthrax-associated death as a consequence of its cytotoxic effects on peripheral macrophages and other cells.

PA acts as a target cell-binding moiety and, after a site-specific N-terminal activation by a cell-associated protease (furin), oligomerises and provides a high-affinity binding component for which EF and LF compete. Following binding of EF or LF to activated PA, the resulting ET or LT complexes become internalised by an acidic endosome compartment, and the toxin factors EF and LF are thereby delivered into the cytosol of the target cell.

EF is a calcium- and calmodulin-dependent adenylyl cyclase that catalyses the conversion of intracellular ATP to cAMP. EF is active in a variety of intracellular signalling pathways, and is thereby capable of disrupting a range of cellular processes LF is a $Zn^{2+}$-dependent metalloprotease that cleaves and inactivates the dual specificity, mitogen-activated protein kinase kinases MAPKK/1 and 2, MEK-1 and MEK-2, and probably other proteins.

A survey of in vitro or in vivo published data on anthrax vaccines for human use indicates the following:—

1. to date, all effective anthrax vaccines contain or produce PA (i.e. either the 83 kDa pro-form, or its activated 63 k Da derivative). In fact, the current dogma is that PA is necessary and sufficient alone to produce an effective anthrax vaccine, and efforts are underway to develop such a vaccine [see, for example, Baillie, L. (2001), 91, pp 609-613];
2. the non-capsulated, toxigenic live-spore vaccines effect a higher degree of protection against all *B. anthracis* strains so far tested than do the licensed cell-free vaccines [see Little, S. F. (1986) Inf. and Immunol. vol. 52, No. 2, pp 509-512];
3. the current cell-free vaccines are generally poorly defined and may vary significantly in effectiveness on a batch-by-batch basis. Accordingly, each batch must be individually tested for efficacy in an animal model prior to human use;
4. the current cell-free anthrax vaccine manufacturing process is evaluated only on completion of the production process and packaging of the final product. Thus, in the event that any one batch of vaccine material should not meet the validation test criteria, the contributing factors cannot be identified readily. Such factors may differ between manufactured batches and the lack of understanding exacerbates any difficulties encountered in the manufacturing process;
5. as a result of the poorly defined nature of current cell-free vaccines, these vaccines may contain quantities of PA together with LF and/or EF which, upon in vivo (or in vitro) activation of PA to the 63 kDa form, may form LT and ET and exert adverse effects on the recipient of the vaccine. Such vaccines may, of course, also contain other *B. anthracis* proteins, both secreted and lysis products, peptidoglycan, nucleic acid and carbohydrate, which may compromise protective efficacy;
6. the current cell-free vaccine compositions are highly variable in terms of LF, PA, and EF concentrations, so much so that EF may be absent from some preparations; and 7. the current cell-free compositions are highly variable in terms of total protein content.

Thus, the concentration of toxin components present in a given composition may vary significantly. This, in turn, may affect efficacy and potential toxicity in humans.

Over the last few years there has been notable academic research in the anthrax field. Sharma et al. (1996) describe the expression of native PA from *E. coli*. The signal sequence of the outer membrane protein A (OmpA) was added to the 5'-end of the PA gene and allowed the purification of the protein from the *E. coli* periplasmic space. Further research has allowed identification of the native binding sites and translocation domain of PA [see Bhatnagas, R. (2001) Critical Rev. in Microbiol., 27(3), pp 167-200; and Batra, S. (2001) Biochem. and Biophys. Res. Comm., 281, pp 186-[92]. Thus, the structure and binding/translocation domains of PA have been well documented.

Recently, a second-generation "recombinant" anthrax vaccine has been proposed by The Ohio State University Research Foundation [see WO 01/45639; and Price, B. M. (2001) Inf. and Immun., vol. 69, No. 7, pp 4509-4515]. The described vaccine is based on PA and LF, wherein the LF molecule has been modified so as to be zinc metalloprotease negative. Thus, the described PA and LF components are fully capable of binding to one another to form an LT molecule, but the resulting LT molecule is not cytotoxic as there is no active zinc metalloprotease function present with the LF component.

Ahuja Nidhi et al., Biochem. and Biophys. Research Communications, Vol. 287, No. 2, 21 Sep. 2001, pp 542-549, describes PA mutants having impaired oligomerization and their potential as vaccine candidates.

Batra Snriti et al., Biochem. and Biophys. Research Communications, Vol. 281, No. 1, 16 Feb. 2001, pp 186-192 describes PA mutants having mutant residues that may have a role in membrane insertion of PA and/or translocation of LF/EF into the cytosol.

WO 02/04646 describes PA polypeptide domains capable of producing an immune response. The PA polypeptide is produced in *E. coli* and accumulates in the form of inclusion bodies.

DNA-based anthrax vaccine compositions are described in WO 2004/024067. The vaccine compositions contain anthrax nucleic acids that have been modified to optimise expression in a eukaryotic host—e.g. the patient to whom the vaccine composition is administered.

In view of the increasing threats of bio-terrorism and biological warfare, there is a need for alternative anthrax vaccines, and for vaccines that address one or more of the above-identified problems.

Thus, according to a first aspect of the present invention, there is provided a polynucleotide sequence comprising a nucleic acid sequence having at least 75% identity to SEQ ID NO: 1, wherein said nucleic acid sequence encodes recombinant *Bacillus anthracis* Protective Antigen (rPA); or a fragment of said nucleic acid sequence wherein said fragment encodes a fragment of recombinant *Bacillus anthracis* Protective Antigen (rPA).

In this regard, SEQ ID NO: 1 represents a modified nucleic acid that encodes rPA. The sequence of SEQ ID NO: 1 is approximately 70% identical to the wild-type *Bacillus anthracis* nucleic acid sequence encoding PA, provided herein as SEQ ID NO: 2.

The present inventors have found that by modifying the wild-type PA nucleic acid sequence (SEQ ID NO: 2), expression levels of rPA protein may be significantly improved. Thus, the present invention relates to non-natural nucleic acid sequences which encode for the rPA polypeptide. Particularly, the non-natural nucleic acid sequences are selected to increase expression levels of rPA expressed in heterologous systems, such as heterologous bacterial systems, e.g. *E. coli*. Preferably, the rPA polypeptide or fragment thereof, which is expressed from the modified, non-natural nucleic acid sequence (or fragment thereof) of the invention, is expressed at a level that is at least 110%, at least 120%, at least 150%, at least 200%, at least 250%, at least 300%, at least 400%, or at least 500% higher than that expressed from the wild-type nucleic acid sequence under equivalent conditions.

The polynucleotide of the invention comprises a nucleic acid sequence (or fragment thereof) that encodes rPA (or a fragment thereof). This rPA encoding nucleic acid sequence (or fragment thereof) is referred to herein as the rPA nucleic acid (or fragment thereof). Thus, the polynucleotide of the present invention may comprise the rPA nucleic acid, plus other coding and/or non-coding sequences. By way of example, non-coding sequences that may be comprised in the polynucleotide of the present invention include promoter sequences and transcription/translation initiation and termination sequences.

In this regard, the rPA nucleic acid sequence of the present invention may embrace a number of modifications, which result in the same translated amino acid sequence of the encoded polypeptide. Numerous factors should be taken into account when modifying a nucleic acid sequence, for example, the degree of degeneracy available, codon usage, and predicted RNA secondary structure considerations. For example, many amino acids are designated by more than one codon, due to the "degeneracy" of the genetic code. In more detail, alanine is coded for by 4 different triplets, and serine is coded for by 6 different triplets. This degeneracy allows for DNA base composition to vary over a wide range without altering the amino acid sequence of the protein encoded by the DNA.

The wild-type polypeptide sequence of *Bacillus anthracis* UM44 PA is provided in SEQ ID NO: 5 (see also, Vodkin, M., et al., Cell, 34:693 (1983); and Welkos, S., et al., Gene, 69(2): 287 (1988)).

For sequence comparison, typically one sequence acts as a reference sequence, to which test sequences may be then compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausubel et al., eds, Current Protocols, a joint venture between Greene Publishing Associates, In. and John Wiley & Sons, Inc. (1995 Supplement) Ausubel].

Examples of algorithms suitable for determining percent sequence similarity are the BLAST and BLAST 2.0 algorithms [see Altschul (1990) J. Mol. Biol. 215: pp. 403-410; and the NCBI (National Center for Biotechnology Information) website].

In one embodiment of a polypeptide homology comparison, the identity exists over a region of the sequences that is at least 10 amino acids, preferably at least 20 amino acids, more preferably at least 35 amino acids in length. In a preferred polypeptide homology comparison, the identity exists over a region of the sequences that is at least 100 amino acids, preferably at least 200 amino acids, more preferably at least 350 amino acids in length.

The terms "peptide" or "polypeptide" throughout this specification are synonymous with the term "protein", and do not refer to a specific length of the product. These terms may embrace post-translational modifications such as glycosylation, acetylation, and phosphorylation.

Reference throughout the present application to rPA polypeptides, polynucleotides and nucleic acids embraces fragments, variants and derivatives thereof.

The term "fragment" of a polypeptide means a peptide consisting of at least 5, preferably at least 10, more preferably at least 20, and most preferably at least 35 amino acid residues of the full-length polypeptide that is the product of the polynucleotide in question. The fragment preferably includes at least one epitope of the corresponding full-length polypeptide. The fragment may result from enzymatic break-down of the corresponding full-length polypeptide. Alternatively, a fragment of the corresponding full-length polypeptide may be produced by expressing a polynucleotide that is fragment of the corresponding full-length polynucleotide.

In preferred embodiments, the polypeptide "fragment" has an amino acid length which is at least 50%, preferably at least 70%, and more preferably at least 80% that of the length of the amino acid sequence of the corresponding full-length polypeptide. For example, the polypeptide fragment may comprise at least 200, preferably at least 300, most preferably at least 400 amino acid residues of the wild-type PA polypeptide sequence (SEQ ID NO: 5).

The present invention embraces "variants". An example of a "variant" is a peptide or peptide fragment that contains one or more analogs of an amino acid (e.g. an unnatural amino acid), or a substituted linkage. In a further embodiment, a "variant" may be a mimic of the peptide or peptide fragment, which mimic reproduces at least one epitope of the peptide or peptide fragment. The mimic may be, for example, a nucleic acid mimic, preferably a DNA mimic.

The present invention also embraces "derivatives", meaning a protein comprising the peptide (or fragment, or variant thereof) in question. Thus, a derivative may include the peptide in question, and a further peptide sequence that may introduce one or more additional epitopes. The further sequence should preferably not interfere with the basic folding and thus conformational structure of the peptide in question.

Examples of a "derivative" are a fusion protein, a conjugate, and a graft. Thus, two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included in a derivative.

All of the molecules "fragment", "variant" and "derivative" have a common antigenic cross-reactivity and/or substantially the same in vitro or in vivo biological activity as the product of the polynucleotide in question from which they are derived. By way of example, an antibody capable of binding to a fragment, variant or derivative would be also capable of binding to the product of the polynucleotide in question.

It is a preferred feature that the fragment, variant and derivative each possess the active site of the peptide in question. Alternatively, all of the above embodiments of a peptide of the present invention share a common ability to induce a "recall response" of a T-lymphocyte which has been previously exposed to an antigenic component of a *Bacillus anthracis* infection.

An rPA peptide fragment, variant or derivative preferably has one or more of the following properties—a) able to bind to the PA receptor on a cell membrane; b) able to bind to EF and/or LF; and c) able to be cleaved by furin protease. Thus, in one embodiment, a fragment, variant or derivative of a peptide of the present invention may be identified by carrying out simple tests for the above-mentioned properties, as described in WO 03/037370 which is incorporated by reference herein.

The terms DNA "fragment", polynucleotide "fragment" and nucleic acid "fragment" used in this application refer to a polynucleotide that will usually comprise at least about 5 codons (15 nucleotides), more usually at least about 7 to 15 codons, and most preferably at least about 35 codons. This number of nucleotides is usually about the minimal length required for a successful probe that would hybridize specifically (e.g. under selective hybridization conditions) with such a sequence.

In preferred embodiments, the DNA "fragment" has a nucleotide length which is at least 50%, preferably at least 70%, and more preferably at least 80% that of the coding sequence of the corresponding gene. For example, the fragment may comprise at least 600, preferably at least 900, most preferably at least 1200 nucleotides of the full-length rPA nucleic acid sequence of the present invention.

The present invention embraces DNA "variants". A DNA variant is a DNA sequence that has substantial homology or substantial similarity to a reference sequence, such as the coding sequence (or a fragment thereof) of the corresponding wild-type (natural) gene. A nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 99% of the nucleotide bases. Homology determination is performed as described supra for peptides.

Alternatively, a DNA "variant" is substantially homologous (or substantially similar) with the coding sequence (or a fragment thereof) of a wild-type (natural) gene when it is capable of hybridizing under selective hybridization conditions. Nucleic acid hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. However, the combination of parameters is much more important than the measure of any single parameter. See, for example, Wetmur and Davidson (1968) J. Mol. Biol. 31:349-370.

Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90% (see, Kanehisa (1984) Nuc. Acids Res. 12: 203-213). The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides. In a preferred embodiment, the length of homology comparison is over a stretch of at least about 170 nucleotides, usually at least about 200 nucleotides, more usually at least about 240 nucleotides, typically at least about 280 nucleotides, more typically at least about 320 nucleotides, and preferably at least about 360 or more nucleotides.

The present invention embraces DNA "derivatives", meaning a DNA polynucleotide which comprises a DNA sequence (or a fragment, or variant thereof) corresponding to the coding sequence of the reference gene, e.g. the wild-type *Bacillus anthracis* PA gene, and an additional DNA sequence which is not naturally associated with the DNA sequence corresponding to the coding sequence. The comments on peptide derivatives supra also apply to DNA "derivatives". A "derivative" may, for example, include two or more coding sequences of an operon. Thus, depending on the presence or absence of a non-coding region between the coding sequences, the expression product(s) of such a "derivative" may be a fusion protein, or separate peptide products encoded by the individual coding regions.

The above terms DNA "fragment", "variant", and "derivative" have in common with each other that the resulting peptide products have cross-reactive antigenic properties, which are substantially the same as those of the corresponding wild-type peptide. Preferably all of the peptide products of the above DNA molecule embodiments of the present invention bind to an antibody which also binds to the wild-type peptide. Alternatively, all of the above peptide products are capable of inducing a "recall response" of a T lymphocyte, which has been previously exposed to an antigenic component of a *Bacillus anthracis* infection.

Thus, a DNA fragment, variant or derivative may be identified by way of its encoded peptide product—for example, by carrying out the simple tests mentioned above (and described in WO 03/037370).

Polynucleotides of the present invention comprise a nucleic acid having at least 75%, preferably at least 80%, more preferably at least 85%, more preferably at least 90%, even more preferably at least 91%, 92%, 93%, 94%, 95%, 96%, 97%, 98% and most preferably 99% or 100% identity to SEQ ID NO: 1; or a fragment of said nucleic acid.

In one embodiment, polynucleotide sequences of the present invention further comprise a polynucleotide encoding a secretion sequence. The polynucleotide encoding the secretion sequence is preferably cloned upstream of the rPA nucleic acid sequence, or fragment thereof, and is most preferably operatively linked to said nucleic acid sequence, or fragment thereof.

Secretion sequences may allow the encoded protein to cross and/or lodge in cell membranes, and thus attain its functional topology or be secreted from a host cell. In this regard, the secretion sequence may be for extracellular translocation of the expressed polypeptide from a host cell (e.g. a bacterial host cell) into the extracellular environment. Alternatively, the secretion sequence may be for periplasmic translocation of the expressed polypeptide from a bacterial host cell cytoplasm into the periplasmic space.

It is particularly preferred that the secretion sequence is cleavable from the expressed polypeptide during periplasmic translocation or during extracellular translocation, in which case the periplasmic/extracellular polypeptide is free of this sequence. One example of such a 'cleavable' sequence is a cpg leader sequence encoded by SEQ ID NO: 3.

The cpg leader sequence illustrated in SEQ ID NO: 3 is designed such that it has a 5'-NdeI restriction site for inserting into an expression vector at a NdeI site, and a 3'-MscI site for fusion with a rPA nucleic acid sequence, or fragment thereof, where a similar MscI site has preferably been engineered. Thus, the cpg leader is cleaved from the expressed rPA protein (or protein fragment) as it passes through a host cell membrane, leaving the 'trimmed' mature rPA protein, or fragment thereof, in the extracellular environment or periplasmic space accordingly.

Other suitable secretion sequences for use in the present invention are described in Watson (1984) Proc. Nat. Acad. Sci. USA. vol. 12: 5145; and Makrides (1996) Microbiological Reviews 60: 512-538; and include, ompA (Denefle et al. (1989) Gene 85: 4990-510; and Ghrayeb et al. (1984) EMBO J. 3: 2437-2442.); pelB (Better et al. (1988) Science 240: 1041-1043; and Lei et al. (1987) J. Bacteriol. 169: 4379-4383); including a degenerate version thereof—see Le Calvez et al. (1996) Gene 170: 51-55; phoA (Denefle et al. (1989) Gene 85: 499-510; and Oka et al. (1985) Proc. Nat. Acad. Sci. USA. 82: 7212-7216); ompT (Johnson et al. (1996) Protein Expression Purif. 7: 104-1123); lamB (Hoffman & Wright (1985) Proc. Nat. Acad. Sci. USA. 82: 5107-5111); ompF (Hoffman & Wright (1985)); beta lactamase (Kadonaga et al. (1984) J. Biol. Chem. 259: 2149-2154; and VIIIa-Komaroff et al. (1977) Proc. Nat. Acad. Sci. USA. 75: 3727-3731); *Staphylococcus aureus* protein A (Abrahmsen (1986) Nucl. Acids Res. 14: 7487-7500; and Macyntyre & Henning (1990) Biochimmie 72: 157-167); *Bacillus subtilis* endoglucanase (Proudfoot et al. (1996) J. Biol. Chem. 271: 2599-2603); murine RNAse (Schein et al. (1992) Biochem. J. 283: 137-144); human growth hormone (Gray et al. (1985) Gene 39: 247-254); and enterotoxins ST-II, LT-A and LT-B (Fujimoto et al. (1988) J. Biotechnol. 8: 77-86; and Morioka-Fujimoto et al. (1991) J. Biol. Chem. 266: 1728-1732).

In one embodiment, the polynucleotide sequence of the present invention comprises a nucleic acid of the present invention, or a fragment thereof, having a 3' and a 5' end, and said nucleic acid or fragment thereof has a codon encoding a methionine residue cloned to the 5' end. By way of example, the nucleic acid may be SEQ ID NO: 7 (or a fragment of SEQ ID NO: 7 that includes the 5' terminal, met-encoding codon of SEQ ID NO: 5). This methionine-encoding codon is added in order to increase stability of the final (signal-less) protein when expressed in *E. coli*. Thus, rPA protein encoded by the polynucleotide of this particular embodiment of the invention is distinguished from wild-type PA protein naturally produced in *Bacillus anthracis* by the addition of an extra methionine residue to the N-terminus.

The present invention thus also provides a polypeptide or polypeptide fragment encoded by the polynucleotide of the present invention. Polypeptides of the present invention may therefore comprise an amino acid sequence encoding rPA, or a fragment thereof, with an extra methionine residue added at the N-terminus of the rPA amino acid sequence.

In a related aspect, the present invention also provides an isolated RNA molecule that is encoded by a DNA polynucleotide sequence of the present invention, or a fragment or variant or derivative of said DNA sequence.

Also contemplated within the invention are expression vectors comprising a polynucleotide of the present invention. Expression vectors are useful for the expression of heterologous nucleic acid sequences in a host cell. As used herein, the term "heterologous" means that the polynucleotide or polypeptide sequence concerned does not naturally exist in the cell, but has been introduced into it, for example by transformation, transfection, injection etc.

Expression vectors generally are replicable polynucleotide constructs that include coding regions for a peptide, operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, "operably linked" means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

It is preferred that the expression vector expresses the polynucleotide in the absence of a chemical inducer—i.e. a chemical inducer is not required for induction of expression from the expression vector. In one embodiment, the vector expresses the polynucleotide constitutively, with no induction of gene expression needed. In another embodiment, the vector expresses the polynucleotide in response to an environmental stimulus or stimuli—such as starvation, or limitation of nutrients or oxygen, such as when a component or components become exhausted in the growth medium.

The term "promoter" is well known in the art, encompasses relatively simple, minimal promoters to complex promoters having upstream elements and enhancers. Suitable promoters for expression in prokaryotic and eukaryotic host cells are well known in the art, and are described in, for example, Molecular Cloning. A laboratory Manual (Sambrook et al., Second edition, 1989) and Current Protocols in Molecular Biology (Ausubel et al., eds., 1994).

Appropriate promoter and other necessary vector sequences are selected so as to be functional in the host. By way of example, promoters such as the trp, lac and phage promoters (e.g. T7, T4, lambda, fd), tRNA promoters and glycolytic enzyme promoters may be used in prokaryotic hosts. It is preferred that the expression vector comprises a "strong" promoter,—i.e. a promoter that is selected so as to ensure that the encoded rPA polypeptide (or fragment thereof) is highly expressed. Examples of strong promoters include recA, malate dehydrogenase, T7, tac, etc. In this regard, a polypeptide is said to be "highly expressed" if it is expressed at levels above 20% of total host cell soluble protein, preferably above 30%, more preferably above 40% and most preferably above 50% total host cell soluble protein. A preferred "strong promoter" for use in accordance with the invention is the malate dehydrogenase (mdh) promoter (proprietary to CAMR; U.S. Pat. No. 5,670,333).

Expression vectors may contain a selectable marker—i.e. a gene encoding a protein necessary for the survival or growth of a host cell transformed with the vector. The presence of this gene ensures the growth on a selective medium of only those host cells that contain the desired vector and that express the selectable marker. Typical selection genes encode proteins that: (a) confer resistance to antibiotics or other toxic substances, e.g. ampicillin, tetracycline, neomycin, methotrexate, etc.; (b) complement auxotrophic deficiencies; or (c) supply critical nutrients not available from complex media. The selection of an appropriate vector and an appropriate selectable marker will depend on the host cell, and is well within the capabilities of an ordinary person of skill in the art.

Expression vectors typically contain all of the additional elements that are necessary for efficient expression of the nucleic acid in a host cell. Examples of suitable vectors for expression of heterologous proteins in bacterial include pET vectors (for example pET26b-Novagen), and pTrKHis (Invitrogen). Both these vectors achieve high-level expression of nucleic acid in *E. coli*.

pMTL expression vectors are advantageous because they are capable of yielding high levels of recombinant protein, and can be very stable, even in the absence of selective pressure using antibiotics. Furthermore, those pMTL vectors based on the very strong *E. coli* malate dehydrogenase (mdh) promoter are particularly advantageous because induction of expression using exogenous inducer chemicals is not required (Alldread et al. (1992) Gene 14: 139-143). It is an advantage not to require an exogenous chemical inducer for regulatory reasons, since any chemical inducer may have to be rigorously and successfully removed from the final product before administration to patients.

In a particularly preferred embodiment, the expression vector is also a high copy number plasmid, such as pMTL1015 (Chambers et al. (1988) Gene 68: 139-149), which was deposited in accordance with the Budapest Treaty on 14 Jun. 2004 and was assigned deposit reference number 04061401 by the European Collection of Cell Cultures (ECACC), Health Protection Agency, Centre for Emergency Preparedness and Response, Porton Down, Salisbury, Wiltshire SP4 0JG UK. pMTL1015 is a derivative of pMTL4, it replicates from a mutant of the ColE1 replicon (600 copies per cell; Minton et al. (1988) Focus 10: 56) and is encoded by SEQ ID NO: 4. Plasmid pMTL1015 is essentially identical to pMTL1003 as described by Brehm et al. (1991) Appl. Microbiol. Biotechnol 36: 358-363, and has numerous advantageous features. By way of example, pMTL1015 differs from pMTL1003 in that the trp promoter has been replaced with the very powerful mdh promoter (Alldread et al. (1992) Gene 14: 139-143), and the ampicillin resistance gene has been replaced with the tetracycline resistance gene of pBR322 (Bolivar et al. (1977). Gene 2: 95). The plasmid also incorporates the pSC101 partition function (par; Miller et al. (1983) Gene 24: 309-315), the mrB double terminator (Brosius et al. (1981) J. Mol. Biol. 148: 107-127) and the pMTL20 polylinker cloning region (Chambers et al., 1988). The par locus endows the plasmid with good segregational stability enabling antibiotic-free fermentations without plasmid loss and the tetracycline resistance marker is a biopharmaceutically acceptable drug.

An example of an expression vector suitable for use in the present invention is the vector deposited under ECACC No: 04061401.

An example of an expression vector comprising a polynucleotide according to the present invention is pMTL1015-cpg-PA-synt, deposited under the Budapest Treaty on 25 May 2005 and accorded ECACC No: 04052501 by the European Collection of Cell Cultures. Health Protection Agency, Centre for Emergency Preparedness and Response, Porton Down, Salisbury, Wiltshire SP4 0JG UK.

The strains E. coli K12 (RV308) pMTL1015-cpg-PA-Synt (ECACC No: 04052501) and E. coli TG1 pMTL1015 (ECACC No: 04061401) were deposited with the European Collection of Cell Cultures (ECACC), Health Protection Agency, Centre for Emergency Preparedness and Response, Porton Down, Salisbury, Wiltshire SP4 0JG UK, on May 25, 2004, and Jun. 14, 2004, respectively, to assure availability of the biological materials to the public.

The vectors containing the nucleic acids of interest can be transcribed in vitro and the resulting RNA introduced into the host cell (e.g. by injection), or the vectors can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). The term "host cells" is meant to embrace the progeny of such cells.

The present application thus also provides a host cell comprising an expression vector as described above. It is preferred that the host cell is a bacterial cell, in particular an E. coli cell, such as E. coli strains DH5, BL21 and HMS174 (Invitrogen).

It is particularly preferred that the bacterial cell e.g. E. coli strain is a protease-deficient strain, since rPA protein is generally considered to be a protease-sensitive protein. One example of a protease-deficient strain of E. coli is E. coli RV308 (ATCC No: 31608).

Also provided by the present invention are methods for producing rPA comprising expressing the polynucleotide of the present invention.

In one embodiment, the polynucleotide is expressed—i.e. transcribed and translated, in a host cell. In another embodiment, the polynucleotide is DNA, which is transcribed into RNA in vitro, and then the RNA is then translated into protein in a host cell. The host cell may be a bacterial cell, such as an E. coli host cell. The E. coli host cell is preferably a protease-deficient strain, such as E. coli RV308 (deposited under ATCC No: 31608).

In a preferred embodiment, rPA is expressed in a host cell from the expression vector of the present invention, as described above. In this embodiment, the method may incorporate at least one, preferably two, most preferably all of the following features:—(i) the expression vector comprises the cpg leader sequence encoded by SEQ ID NO: 3; (ii) the vector is the plasmid pMTL1015, encoded by SEQ ID NO: 4; and (iii) the vector is expressed in an E. coli host cell such as E. coli RV308 (ATCC No: 31608).

In one embodiment, the method comprises the initial steps of transforming an expression vector comprising the polynucleotide of interest into a host cell, such as E. coli host cell and culturing the transformed host cell in a suitable growth medium.

Optionally, the culture is carried out under selective pressure, such as in the presence of an antibiotic, e.g. tetracycline, in which case it is an advantage for the expression vector to comprise a selectable marker that confers resistance to the antibiotic.

Culture parameters may be controlled, in order to control nutrients, pH and/or oxygen levels (dissolved oxygen tension—DOT) in the culture. For example, DOT may be controlled by agitation, back pressure, sparged airflow and/or oxygen supplementation. It is preferred that DOT is maintained at above 40%.

The temperature at which host cells are grown can have an effect on the level of protein that can be purified from the culture. For example, protein expression rate and protein degradation rate (such as due to protease activity) can both affect the amount of protein that can be extracted. Growing the cultured host cells comprising the claimed polynucleotide at a reduced temperature of less than, for example 40° C., has been found to give acceptable levels of rPA expression and stability. Thus, in one embodiment of the invention, host cells containing polynucleotides of the invention (e.g. expression vectors) are cultured at less than 40° C.; preferably at less than 37° C.; more preferably at less than 35° C.; more preferably at about 30° C., and most preferably at 25-30° C., such as 29° C., 28° C., 27° C., 26° C. and 25° C. Culturing host cells at these reduced temperatures may slow down the rate of rPA expression, but this may be useful if a high-level expression vector, such as the plasmid pMTL1015, is used for expression.

It is preferred that a growth medium is used that is free of animal products (i.e. products derived from animals), since this is advantageous for meeting the regulations for injectable products. Examples of suitable media include phytone peptone—based Terrific Broth, and soy peptone-based L-broth.

If a secretion sequence is used that enables extracellular secretion of the polypeptide into the growth medium then the growth medium may be harvested and undergo further purification steps to extract the polypeptide.

Alternatively, if the secretion sequence enables secretion of the polypeptide into the bacterial periplasm then the polypeptide product will be intracellular. In this case, the cells must be harvested from the culture medium (e.g. by centrifugation as a cell paste) and undergo further processing to extract the polypeptide from the cells. Suitable protocols for the harvesting of cell cultures, such as bacterial cultures, for the purification of polypeptides are well known in the art, and can be found in common laboratory manuals such as Sambrook et al. (1989) Molecular Cloning: A Laboratory Manual, Second Edition, Cold Spring Harbor Laboratory Press; and Sambrook and Russell (2001) Molecular Cloning: A Laboratory Manual, Third Edition, Cold Spring Harbor Laboratory Press.

Typically, bacterial cells can be harvested by centrifugation for extraction of either nucleic acids or polypeptides. For protein purification the conditions selected for the harvesting of cultured cells by centrifugation are generally gentler than for the extraction of nucleic acid, so as not to damage the target protein. For example, the harvesting of bacterial cells for extraction of a target polypeptide may be carried out at 4° C., by centrifugation at 4,000-5,000 g for 10-15 minutes.

It is an option for the method to further comprise testing steps, to identify the presence and/or yield of desired polypeptide, prior to further processing. In one embodiment, an ELISA-based test is carried out.

Following the fermentation (bacterial growth and harvesting) and optional testing protocols, the method may further comprise downstream processing steps in order to obtain isolated, purified, rPA protein.

The downstream processing steps employed in the present invention preferably achieve one or more of the following aims:— reduction in the number of chromatography steps required, compared to prior art methods;

use of step elution rather than gradient elution for some, preferably all, chromatography steps;

increase in the level of primary processing prior to chromatography, compared to prior art methods;

removal of the need for the addition of conditioning agents (e.g. nucleases) where possible;

use of techniques capable of scaling-up to at least 100 L fermentation scale; and use of techniques that are compatible with cGMP.

It is preferred that the purification procedure has reduced process times and volumes and/or has increased process efficiency in comparison to prior art methods. In the present invention, the number of dialysis/buffer exchange steps is preferably minimised, for example, by linking steps that generate a process stream of high conductivity with those that require a high conductivity starting material (e.g. ammonium sulphate precipitation or ion-exchange chromatography may be followed by hydrophobic interaction chromatography).

The downstream processing protocol commences with a crude mixture containing rPA polypeptide. If the rPA polypeptide is located within the host cell (e.g. within a bacterial host cell periplasm) then the cells must be treated to extract the rPA polypeptide, for example by homogenisation.

It is preferred that the method further comprises at least one separation step, carried out on the extracted rPA polypeptide. Examples of separation steps that may be included in the method are filtration steps such as diafiltration steps, and chromatography steps. In one embodiment, the method comprises at least one chromatography step and at least one filtration step.

In a particularly preferred embodiment of the present method, the extracted rPA polypeptide (together with unwanted components such as nucleic acids, other proteins, and cell debris) is subjected to diafiltration, such as tangental flow diafiltration. The purpose of this step is to alter the load of charged molecules, in preparation for subsequent separation steps, such as chromatography steps. Diafilters retain molecules of above a certain molecular weight (e.g. above 30 kDa, 40 kDa or 50 kDa) and allow dissolved substances and those below the specified molecular weight to pass through the filter. Thus, it is preferred that the method includes at least one filtration step that is a diafiltration step.

Chromatography steps may include ion-exchange chromatography (e.g. using a Q-sepharose anion exchange column) and hydrophobic charge chromatography (e.g. using a mercaptoethyl pyridine hypercel column). Other examples of suitable chromatographic techniques are known in the art and would be routinely available to a skilled person. Thus, the present method may include at least one ion-exchange chromatography step and at least one hydrophobic charge chromatography step.

In one embodiment, when the rPA polypeptide has been expressed in an *E. coli* host cell, there may be residual *E. coli* endotoxin associated with the rPA polypeptide and this can be separated from the rPA polypeptide by a (further) separation step, if necessary. In one embodiment, separation of endotoxin may be achieved by filtration, using a charged filter to which the toxin adheres.

Thus, in a specific embodiment, a method of producing rPA comprises the steps of obtaining host cells that express the polypeptide of the present invention; extracting the expressed rPA from the host cells; subjecting the extracted rPA to a diafiltration step (e.g. tangental flow diafiltration at 30 kDa); followed by at least one chromatography step selected from ion exchange chromatography and hydrophobic charge chromatography; then a further diafiltration step (which may be at a higher molecular weight cut-off e.g. 40 kDa or 50 kDa); and an optional further filtration step to remove any residual protein and/or bacterial endotoxin.

In one embodiment of the present invention, the combination of high-level gene expression (plasmid containing strong promoter), periplasmic translocation (secretion sequence), nucleic acid sequence modification (rPA nucleic acid sequence) and efficient downstream processing, results in an increase of rPA protein yields that are 10 to 20-fold above yields previously available in the prior art.

Furthermore, the downstream processing steps of the present invention allow rPA protein to be obtained that has greater than 70%, preferably greater than 80%, greater than 90%, or greater than 95%, and more preferably greater than 98% purity.

Polypeptide purity or homogeneity may be indicated by, for example, polyacrylamide gel electrophoresis of a protein sample, followed by visualizing a single polypeptide band upon staining the gel. Alternatively, higher resolution may be provided by using, for example, HPLC.

If desirable, the amino acid sequence of the polypeptides of the present invention may be determined by protein sequencing methods.

The present invention thus also provides an rPA polypeptide or fragment thereof produced by the method of the present invention. In one embodiment, the polypeptide may be identical to wild-type PA produced by *Bacillus anthracis*. In another embodiment, as described above, the polypeptide or fragment thereof may be distinguished from wild-type PA (or a fragment thereof) by the presence of an extra residue, such as a methionine residue, at the N-terminus of the rPA amino-acid sequence. For example, the polypeptide may be SEQ ID NO: 6, or a fragment thereof comprising the N-terminal methionine residue of SEQ ID NO: 6.

Also envisaged by the present invention is a kit, which may comprise one or more of a polynucleotide, an expression vector, a host cell, and a polypeptide of the present invention.

Also provided by the present invention are antigenic compositions, such as vaccine compositions, comprising a polypeptide according to the present invention.

The invention also provides methods of inducing an immune response against infection by *Bacillus anthracis* comprising administering a polypeptide of the present invention or an antigenic composition of the present invention.

Also provided by the present invention is use of a polypeptide of the present invention for manufacture of a medicament for inducing an immune response against infection by *Bacillus anthracis*.

In this regard, "inducing an immune response" may embrace protecting against infection by *Bacillus anthracis*. The protection conferred by the method and/or use of the present invention may be 100%, or may be less than 100%. Preferably, "protecting against infection by *Bacillus anthracis*" provides protection against at least 50%, preferably at least 70%, more preferably at least 80%, most preferably at least 90%, 91%, 92%, 93%, 94%, 95%, 96%, 97%, 98% or 99% of *Bacillus anthracis* infections. Preferably, "protecting against infection by *Bacillus anthracis*" provides a level of protection that is at least 50%, preferably at least 70%, more preferably at least 80%, most preferably at least 90%, 91%, 92%, 93%, 94%, 95%, 96%, 97%, 98% or 99% effective against a *Bacillus anthracis* infection.

Furthermore, the term "protecting against infection" may embrace preventing infection and treating infection. In this regard, the term "preventing" includes reducing the severity/intensity of, or initiation of, a *Bacillus anthracis* infection. The term "treating" includes post-infection therapy and amelioration of a *Bacillus anthracis* infection.

The antigenic composition may be administered by conventional routes, e.g. intravenous, subcutaneous, intraperitoneal, and mucosal routes using methods well known in the art.

Typically, such antigenic compositions are prepared as injectables, either as liquid solutions or suspensions; solid forms suitable for solution in, or suspension in, liquid prior to injection may also be prepared. The preparation may also be emulsified, or the peptide encapsulated in liposomes or microcapsules.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy phosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The active components may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The antigenic compositions are conventionally administered parenterally, by injection, for example, either subcutaneously or intramuscularly.

The antigenic compositions are for administration in a manner compatible with the dosage formulation, and in such amount as will be prophylactically and/or therapeutically effective. The quantity to be administered, which is generally in the range of 5 micrograms to 250 micrograms of antigen per dose, preferably about 50-100 µg per dose, depends on the subject to be treated, capacity of the subject's immune system to synthesize antibodies, and the degree of protection desired. Precise amounts of the active ingredient that is required to be administered may depend on the judgment of the practitioner and may be particular to each subject.

The antigenic composition may be given in a single dose schedule, or optionally in a multiple dose schedule. A multiple dose schedule is one in which a primary course of vaccination may be with 1-6 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the antigenic composition containing the immunogenic antigen(s) may be administered in conjunction with other immunoregulatory agents, for example, immunoglobulins, as well as antibiotics.

Additional formulations which are suitable for other modes of administration include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

In one embodiment the medicament may be administered intranasally (i.n.). An intranasal composition may be administered in droplet form having approximate diameters in the range of 100-5000 µm, which in terms of volume would have droplet sizes in the approximate range of 0.001-100 µl.

Intranasal administration may be achieved by way of applying nasal droplets or via a nasal spray. In the case of nasal droplets, the droplets may typically have a diameter of approximately 1000-3000 µm and/or a volume of 1-25 µl, whereas in the case of a nasal spray, the droplets may typically have a diameter of approximately 100-1000 µm and/or a volume of 0.001-1 µl.

It is possible that, following i.n. delivery of antibodies, their passage to the lungs may be facilitated by a reverse flow of mucosal secretions.

In a different embodiment, the medicament may be delivered in an aerosol formulation. The aerosol formulation may take the form of a powder, suspension or solution.

The size of aerosol particles is one factor relevant to the delivery capability of an aerosol. Thus, smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli.

The aerosol particles may be delivered by way of a nebulizer or nasal spray.

In the case of aerosol delivery of the medicament, the particles may have diameters in the approximate range of 0.1-50 μm, preferably 1-5 μm.

The aerosol formulation of the medicament of the present invention may optionally contain a propellant and/or surfactant.

By controlling the size of the droplets which are to be administered to a patient to within the defined range of the present invention, it is possible to avoid/minimise inadvertent antigen delivery to the alveoli and thus avoid alveoli-associated pathological problems such as inflammation and fibrotic scarring of the lungs.

Intranasal vaccination engages both T and B cell mediated effector mechanisms in nasal and bronchus associated mucosal tissues, which differ from other mucosae-associated lymphoid tissues.

Intranasal delivery of antigens allows targeting of the antigens to submucosal B cells of the respiratory system. These B cells are the major local IgA-producing cells in mammals and intranasal delivery facilitates a rapid increase in IgA production by these cells against the anthrax antigens.

In one embodiment administration of the medicament comprising an anthrax antigen stimulates IgA antibody production, and the IgA antibody binds to the anthrax antigen. In another embodiment, a mucosal and/or Th2 immune response is stimulated.

In one embodiment, the vaccine composition comprises rPA protein adsorbed to Alhydrogel™ adjuvant. In one embodiment, the vaccine is delivered by intramuscular injection.

The invention also provides a vector having the sequence SEQ ID NO:4.

The invention also provides a vector as deposited under ECACC No: 04061401.

The invention also provides a vector comprising a polynucleotide according to the present invention, as deposited under ECACC NO: 04052501.

1. Blank.

2. rPA Standard (DEV0301P; 100 μg/mL)

Figure 1:
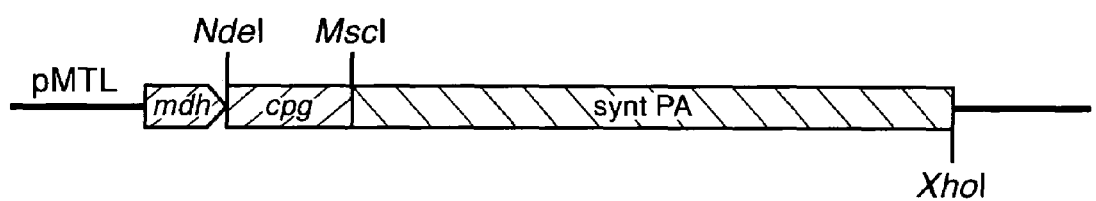
FIG. 1 depicts HPA clone pMTL1015-cpg-rPA-synt—i.e. the modified rPA nucleic acid sequence fused to the $cpg_2$ leader in pMTL1015 (TcR). Manipulations required to generate this plasmid are as follows: (1) sub-clone synthetic 'mature' rPA sequence from sequence verified PCR product TOPO vector (i.e. without any leader) into HPA pET22bcpg vector; (2) sub-clone cpg-SynPA from pET22bcpgSynPA into pMTL1015.
Figure 2:
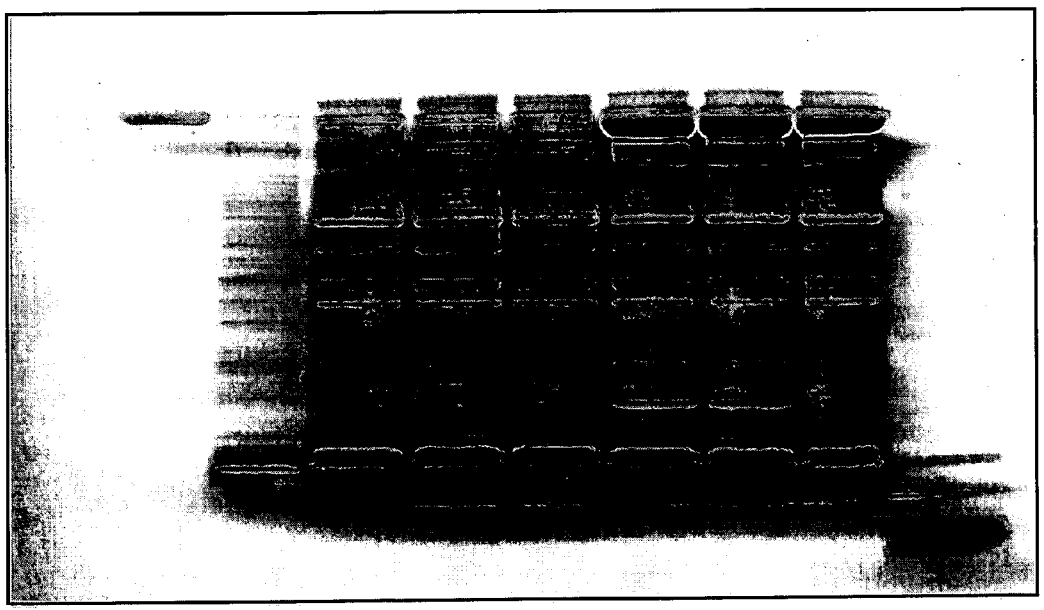
FIG. 2 demonstrates SDS-PAGE of pMTL1015 clones expressing rPA after 16 hr Shake-flask culture in phytone peptone-based Terrific Broth. The key is as follows:—
Figure 3:
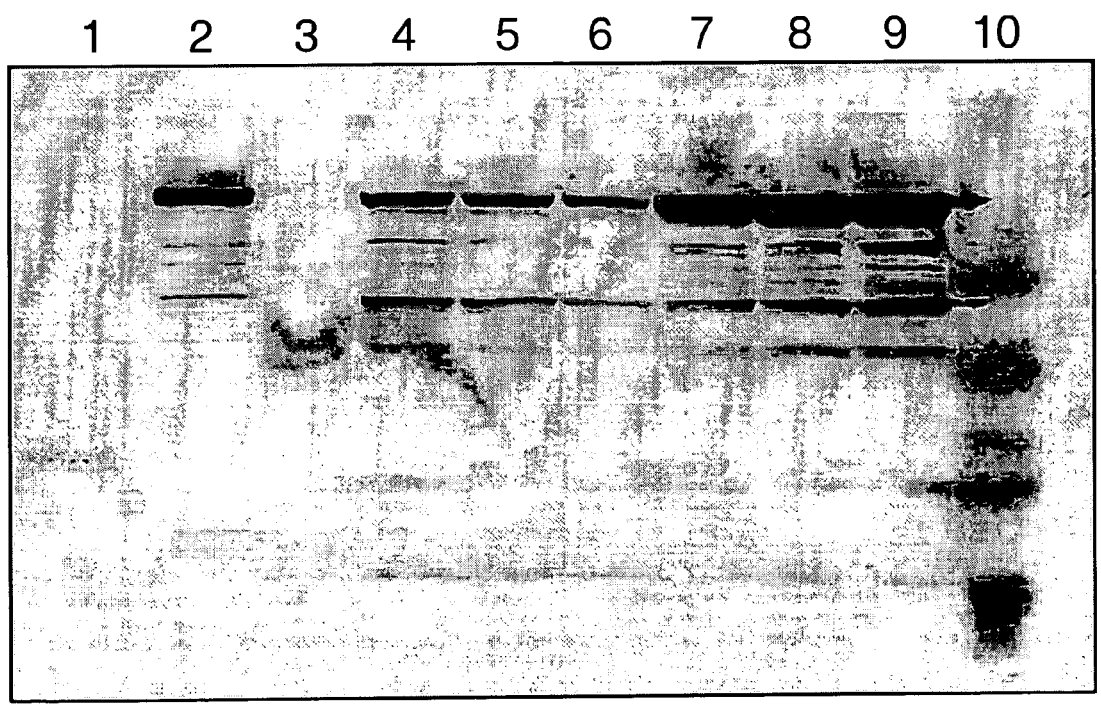

3. pMTL1015 vector only 4. pMTL1015-ompA-PA-wt 5. pMTL1015-cpg-PA-wt 6. pMTL1015-pelB-PA-wt 7. pMTL1015-ompA-PA-synt 8. pMTL1015-cpg-PA-synt 9. pMTL1015-pelB-PA-synt 10. Molecular weight markers FIG. 3 shows a Western blot of pMTL1015 clones expressing rPA after 16 hrs Shake-flask culture in phytone peptone-based Terrific Broth. The key is as described above for FIG. 2.

Figure 4A:
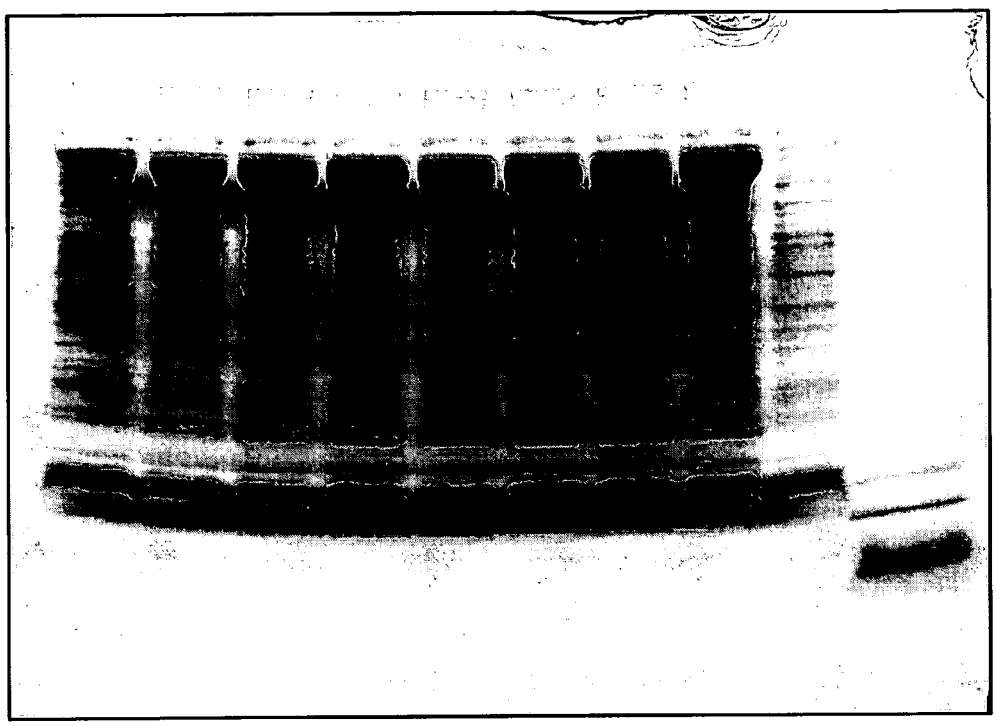
Figure 4B:
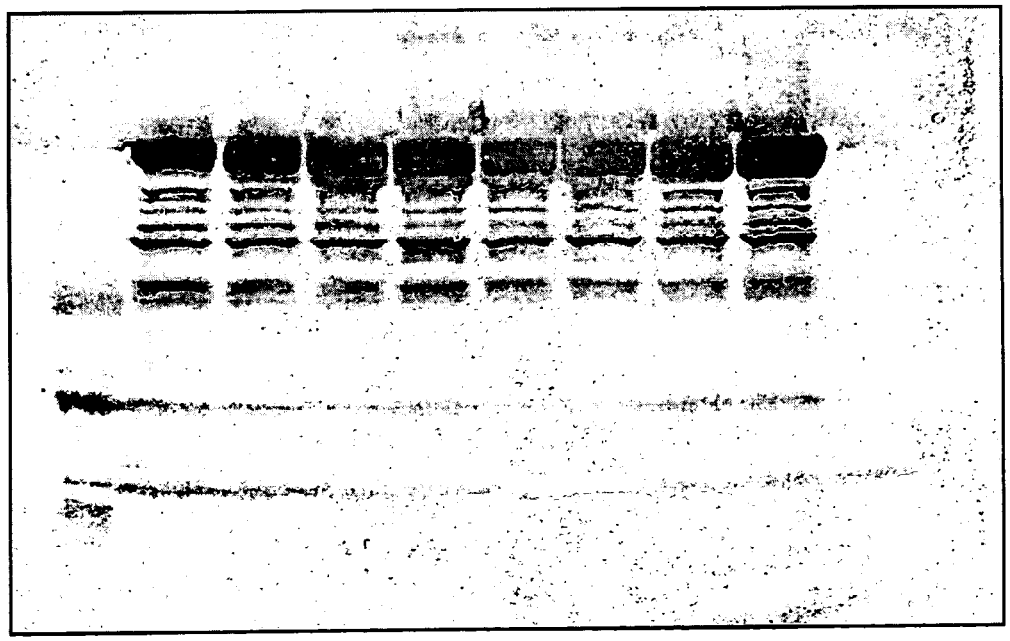

FIG. 4 shows time course analysis by (A) SDS-PAGE and (B) Western Blot of samples from Shake-flask culture of *E. coli* (pMTL1015-cpg-PA-synt) in phytone peptone-based Terrific Broth. The negative control was *E. coli* RV308 (pMTL1015).

FIG. 5 shows growth curves of *E. coli* RV308 pMTL1015-ompA-PA-synt in phytone peptone-based Terrific Broth, Shake-flask culture, in baffled flasks (A and B) or non-baffled flasks (C).

FIG. 6 shows growth curves of *E. coli* RV308 pMTL1015-ompA-PA-wt (A and B) and pMTL1015-ompA-PA-synt [C and D) in Hy-soy based semi-defined medium, Shake-flask culture.

Figure 7:
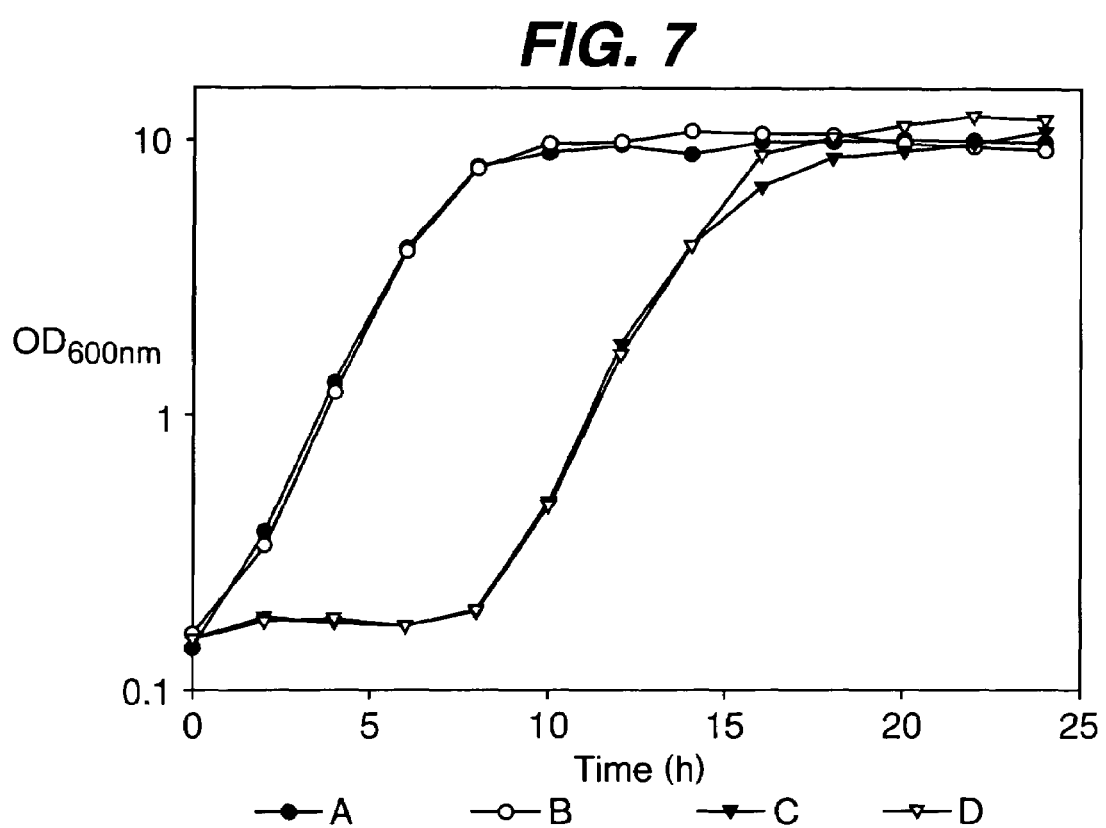

FIG. 7 shows growth curves of *E. coli* RV308 pMTL1015-pelB-PA-wt (A and B) and pMTL1015-pelB-PA-synt [C and D) in Hy-soy based semi-defined medium, Shake-flask culture.

Figure 8:
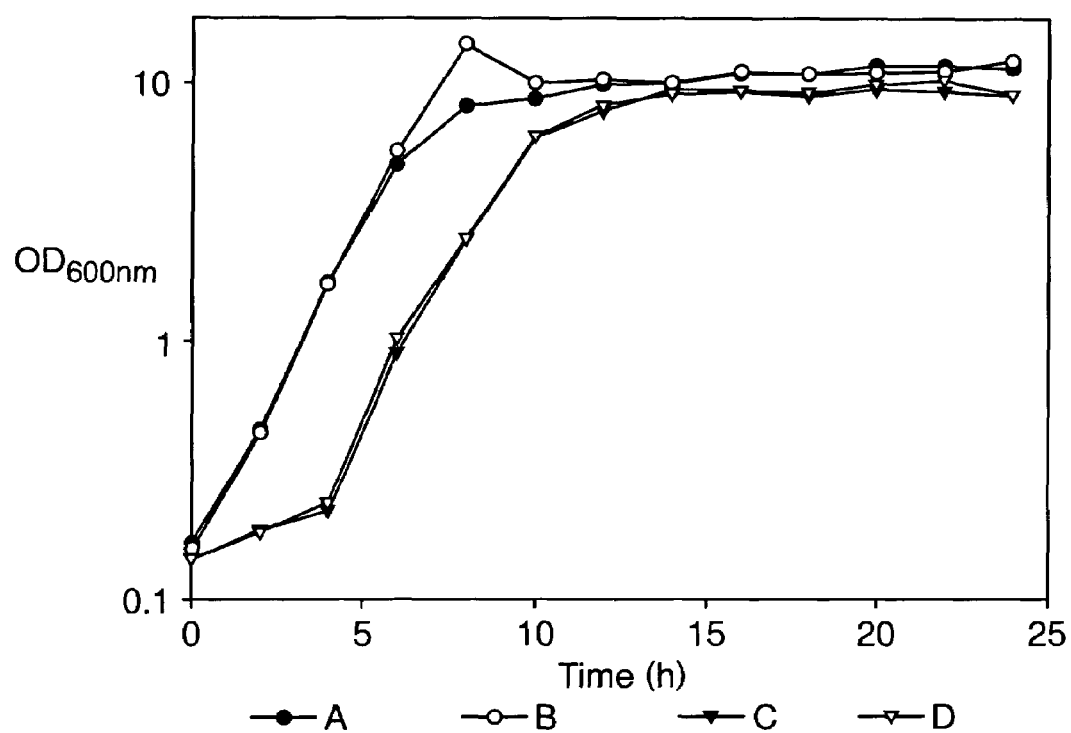

FIG. 8 shows the growth curve of *E. coli* RV308 pMTL1015-cpg-PA-wt (A and B) and pMTL1015-cpg-PA-synt [C and D) in Hy-soy based semi-defined medium, Shake-flask culture.

Figure 9:
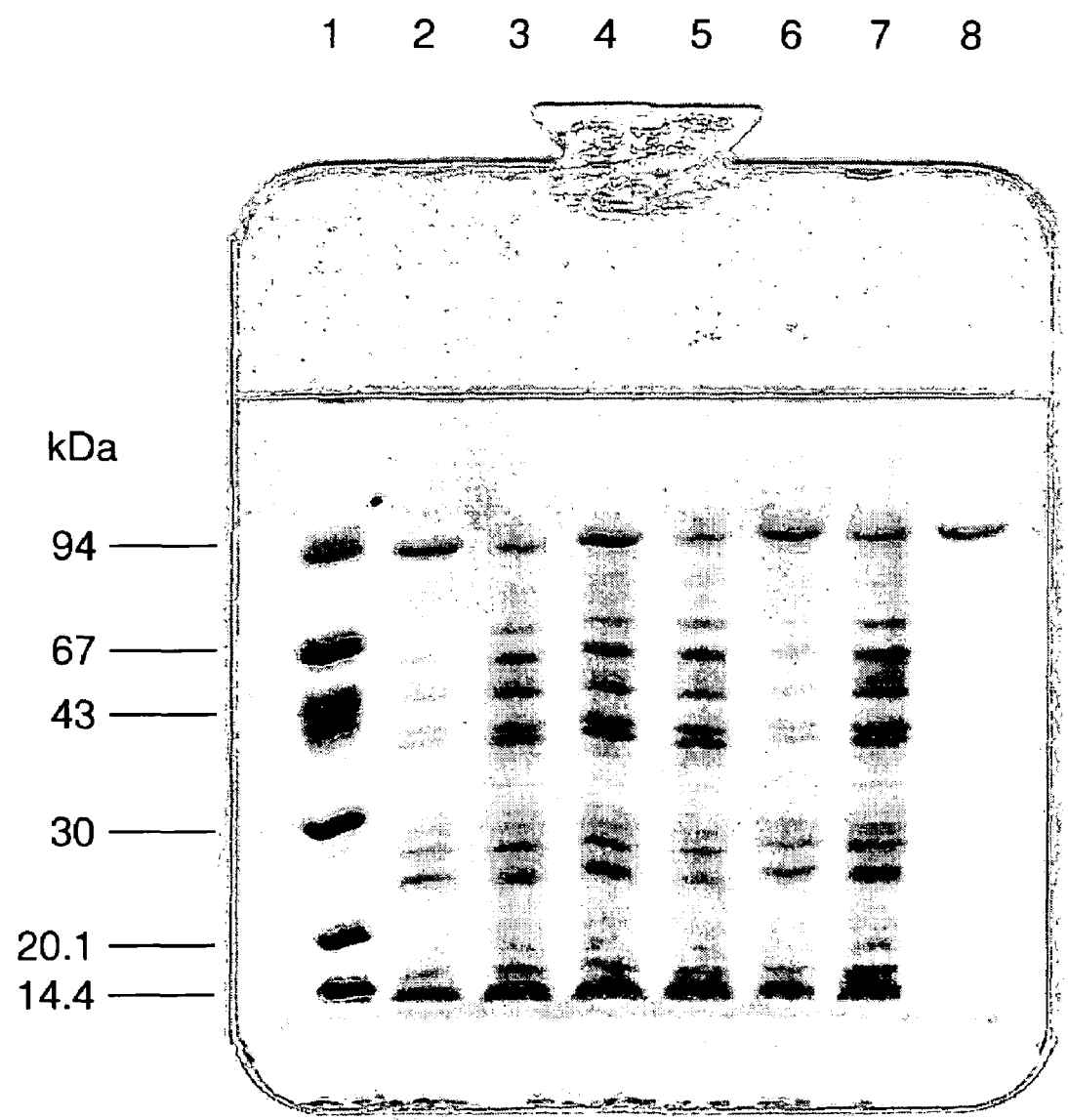

FIG. 9 shows SDS-PAGE (12.5% PHAST-GEL) of pMTL1015 clones expressing rPA in Shake-flask culture using Hy-soy based semi-defined medium. The key is as follows:—

1: Molecular Weight Markers

2: RV308 pMTL1015 ompA-PA-synt

3: RV308 pMTL1015 ompA-PA-wt

4: RV308 pMTL1015 pelB-PA-synt

5: RV308 pMTL1015 pelB-PA-wt

6: RV308 pMTL1015 cpg-PA-synt

7: RV308 pMTL1015 cpg-PA-wt

8: Reference DEV03031P (100 μg/mL)

Figure 10:
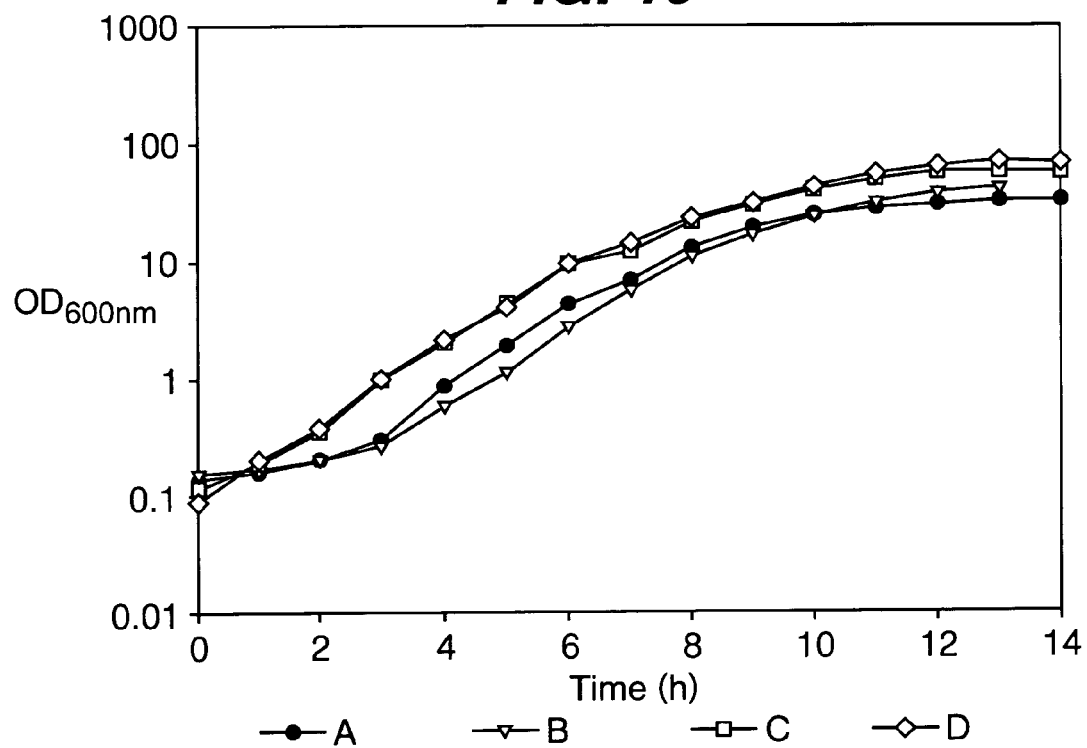

FIG. 10 shows growth of *E. coli* RV308 pMTL1015-cpg-PA-synt in production medium (Phytone peptone 12 g/L, Bacto yeast extract 60 g/L, glucose 25 g/L, magnesium sulphate heptahydrate 2 g/L, $K_2HPO_4$ 12.54 g/L, $KH_2PO_4$ 2.31 g/L and tetracycline 1.5 mg/L, pH 7.0-7.2), with varying levels of Yeast Extract, as follows:—

A 1× yeast extract

B 1.5× yeast extract

C 2× yeast extract

D 2.5× yeast extract

Figure 11:
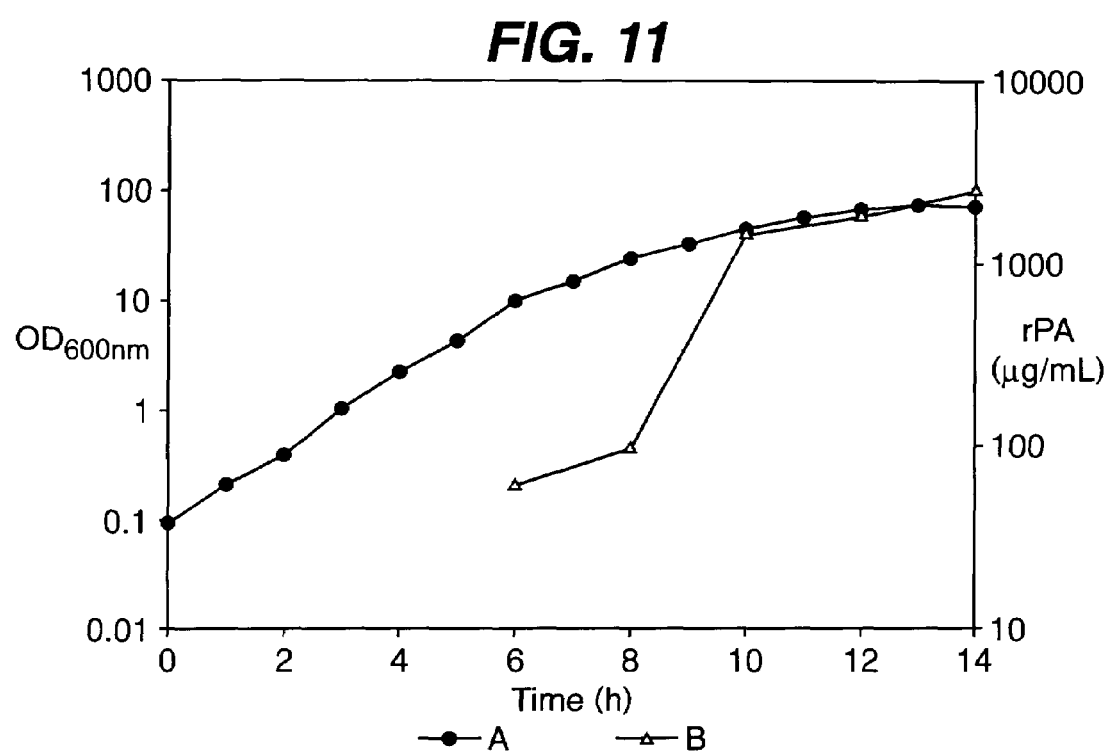

FIG. 11 shows growth curves (A) and rPA production curves (B) for *E. coli* RV308 pMTL1015-cpg-PA-synt in production medium.

Figure 12:
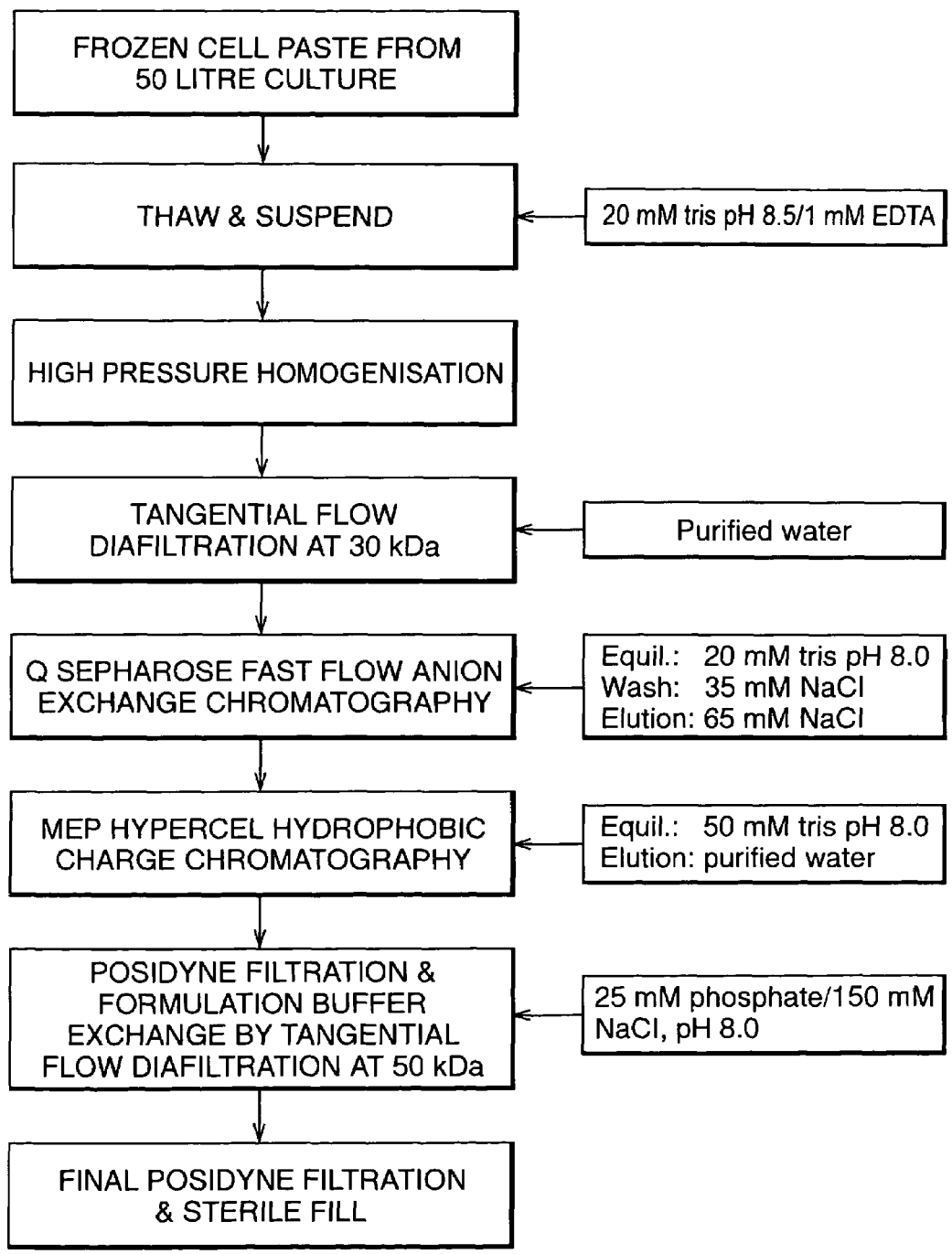

FIG. 12 is a flow chart showing the downstream processing steps for isolation of rPA.

Figure 13:
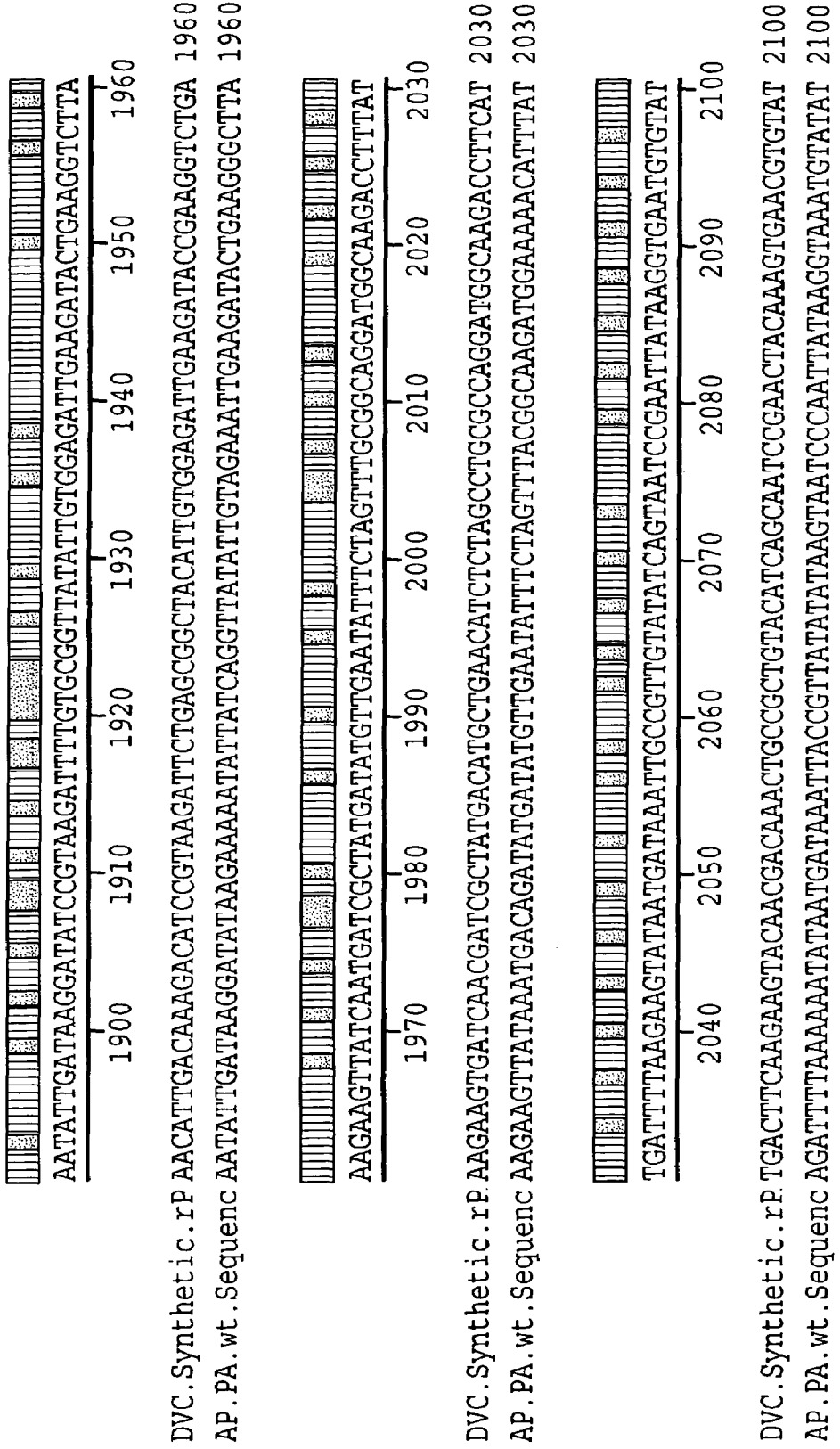

FIG. 13 (A-D) shows the sequence alignment between SEQ ID NO: 8"DVC.Synthetic.rP" (i.e. the wild-type PA gene sequence, SEQ ID NO: 2, plus a 5' codon encoding a methionine residue), and SEQ ID NO: 7—"AP.PA.wt.Sequenc" (i.e. the modified rPA gene sequence of the present invention, SEQ ID NO: 1, plus a 5' codon encoding a methionine residue). The sequence identity is 71.2% (the consensus sequence is disclosed as SEQ ID NO: 9).

EXEMPLIFICATIONS

The invention is now described by reference to the following Examples.

Example 1 rPA Expression Systems pMTL expression vector constructs were generated, directing expression of either the wild-type PA gene sequence or the modified rPA gene sequence, fused to either the *Erwinia carotovora* pelB or the pseudomonad carboxypeptidase $G_2$ ($cpg_2$) leader sequences. The latter sequence is described in European Patent 0 121 352, and has been shown to be efficiently processed in *E. coli*, directing soluble protein into the periplasmic space. These rPA expression constructs were compared with Dynport Vaccine Company (DVC)'s pET26b and Invitrogen pTrk vector-based constructs for evaluation.

Generation of novel rPA pMTL-based expression clones was as follows:

PCR amplification of the two PA-encoding nucleotide sequences (wild type and modified) fused to both the pelB, ompA and $cpg_2$ leader sequences. This generated six rPA sequence options.

Primary clones were constructed in a PCR product cloning vector system (e.g. Invitrogen TA Cloning).

Primary clones were authenticated by DNA sequence analysis of the composite PA/leader sequences.

The six rPA sequences were sub-cloned into pMTL1015 expression vector and the recombinant plasmids were authenticated.

Plasmid DNA derived from the four authenticated clones was used to transform a protease-deficient expression strain, *E. coli* RV308 (ATCC 31608).

Strategy for Comparison of rPA Expression Systems

The six clones based on the pMTL expression plasmid were evaluated in shake-flask culture in the current production medium. The existing DVC production organism was used as a control. Growth conditions and induction initiation/duration (where applicable) were standardised as much as possible to allow a true comparison of expression levels to be made under the given experimental conditions. For example, a standard cell density was used for inoculation. Production levels were compared by sampling cultures throughout growth and following chemical cell lysis using BugBuster™ (Novagen) of harvested cells, by densitometric analysis of SDS-PAGE. Western blotting was used to confirm the identity of the rPA protein band.

Media Selection Strategy

In addition to increasing the expression level of rPA by genetic manipulation, the final yield of product was raised by growing cultures to a higher cell density using a medium containing higher nutrient levels.

The strains showing the most promise in terms of rPA production levels in the current production medium were examined further, initially in shake-flask culture, using a range of potential production media. The analytical techniques used by DVC (SDS-PAGE, RP-HPLC) were used to estimate product levels throughout growth and at harvest.

Example 2

Shake-Flask Comparisons of rPA Expression

Example 2.1

Phytone Peptone-Based Terrific Broth

An experiment was performed to compare the expression of rPA by six pMTL1015 clones in phytone peptone-based Terrific Broth using shake-flask culture. Since previous work using the pMTL1015 expression system at CAMR had shown that low oxygenation rates may favour product expression, cultures were set up in both baffled flasks (high oxygenation) and non-baffled flasks (low oxygenation).

The 10 mL cultures prepared as primary seed cultures for the cell banking were used to prepare seed cultures for this study. A 50 μL aliquot of the 10 mL culture was used to inoculate 50 mL of phytone peptone-based Terrific Broth in 250 mL baffled flasks. These seed cultures were incubated at 30° C. at 150 rpm for 17 h and then used to inoculate duplicate 200 mL cultures of the same medium in 1000 mL baffled flasks and single cultures of 250 mL in 500 mL non-baffled flasks. The inoculum for each culture was calculated to give a starting $OD_{600}$ of 0.1-0.2. The cultures were incubated at 30° C. and 150 rpm for 24 h. Samples (2.5 mL) were removed at 2 hourly intervals for rPA assay when the $OD_{600}$ reached 5-7. Samples were centrifuged at 4,000 rpm in a Clandon T-52 bench top centrifuge for 15 min, the supernatant decanted and the pellets stored frozen at −20° C. After 24 h growth, the duplicate baffled flask cultures were bulked and the cell mass harvested by centrifugation (Sorvall RC-3, 5000 rpm for 15 min) and the cell paste stored frozen at −20° C.

FIGS. 2 and 3 show SDS-PAGE and Western blot analysis of the 16 h samples from each of the pMTL1015 clones grown in phytone peptone-based Terrific Broth under conditions of high oxygenation (baffled flasks) following treatment with BugBuster™. It can be seen that strong protein bands are present at the expected rPA molecular mass following SDS-PAGE for the three clones expressing the synthetic gene product, with weaker bands for those clones expressing the wild type gene (FIG. 2). The amount of rPA present was estimated by comparison with the intensity of the rPA standard and confirmed by ELISA (Table 1). The Western blot analysis demonstrated the presence of some immuno-reactive material at lower molecular weights than the rPA (FIG. 3). The amount of this material relative to intact rPA was similar for all clones. It is not known at present whether this represents proteolytic degradation products or truncated expression.

TABLE 1

Comparison of rPA expression of all 12 *E. coli* clones following growth in phytone peptone-based Terrific Broth.

| | | | | rPA (μg/mL culture) | |
|---|---|---|---|---|---|
| Clone | Name | *E. coli* host | $OD_{600}$ culture | *Gel estimate | ELISA |
| 1 | pET26b-PA | BL21 (DE3) | 5.5 | <100 | 24 |
| 2 | pET26b-PA-synt | BL21 (DE3) | 3.6 | <100 | 11 |
| 3 | pTrck-pelB-PA | DH5a | 9.7 | <100 | 57 |
| 4 | pTrck-ompA-PA | DH5α | 9.7 | <100 | 74 |

TABLE 1-continued Comparison of rPA expression of all 12 E. coli clones following growth in phytone peptone-based Terrific Broth.

| Clone Name | | E. coli host | OD$_{600}$ culture | *Gel estimate | rPA (μg/mL culture) ELISA |
|---|---|---|---|---|---|
| 5 | pMTL1015-pelB-PA-wt | RV308 | 17.3 | <100 | 58 |
| 6 | pMTL1015-ompA-PA-wt | RV308 | 19.7 | <100 | 135 |
| 7 | pMTL1015-cpg-PA-wt | RV308 | 20.4 | <100 | 67 |
| 8 | pMTL1015-pelB-PA-synt | RV308 | 21.1 | >>100 | 394 |
| 9 | pMTL1015-cpg-PA-synt | RV308 | 23.3 | >>100 | 496 |
| 10 | pMTL1015-ompA-PA-synt | RV308 | 25.3 | >>100 | 476 |
| 11 | pTrck-pelB-PA-synt | DH5α | 8.2 | >100 | 304 |
| 12 | pTrck-ompA-PA-synt | DH5α | 11 | >100 | 252 |

*estimate of rPA concentration from SDS-PAGE by comparison with 100 μg/mL rPA standard.

Time course samples from the pMTL1015-cpg-PA-synt clone were analysed by SDS-PAGE (Phast-gel), Western Blot (FIG. 4) and ELISA (Table 2) to determine; (a) the point at which rPA expression was maximal, and (b) whether prolonged incubation resulted in loss of product due to proteolytic activity. It can be seen that rPA expression by ELISA was optimal after 14-16 h incubation and did not change appreciably with further incubation up to 24 h (Table 2). Western blot analysis (FIG. 4) showed that the level of lower molecular weight immuno-reactive material relative to intact rPA did not change significantly with extended incubation time.

TABLE 2

Time course analysis by ELISA of samples from shake flask culture of E. coli (pMTL1015-cpg-PA-synt) in phytone peptone based Terrific Broth.

| Time (h) | rPA (μg/mL culture) |
|---|---|
| 10 | 107 |
| 12 | 313 |
| 14 | 507 |
| 16 | 532 |
| 18 | 488 |
| 20 | 491 |
| 22 | 487 |
| 24 | 525 |

FIG. 5 shows the growth curves obtained for E. coli RV308 (pMTL1015-ompA-PA-synt) when grown in phytone peptone-based Terrific Broth using baffled (high oxygenation) and non-baffled (low oxygenation) flasks. It can be seen that growth was substantially better in the baffled flasks. Cultures grown in non-baffled flasks reached a much lower final cell density compared with the baffled flask cultures. rPA expression was considerably lower in the cultures grown in non-baffled flasks (data not shown).

Example 2.2

Hy-Soy-Based Semi-Defined Medium

The experiment described above (Example 2.1) was repeated using Hy-Soy based semi-defined medium in baffled flasks only. The growth curves (FIGS. 6, 7 & 8) show that lower growth rates and final cell densities were obtained in this medium compared to Terrific Broth and a lag phase of up to 8 h was obtained for the clones expressing the synthetic gene. rPA expression levels were generally lower than observed in phytone peptone-based Terrific Broth; however, a similar pattern of superior expression levels with clones expressing the synthetic gene compared with the wild-type gene was observed by SDS-PAGE (FIG. 9) and ELISA (Table 3).

TABLE 3

Comparison of rPA expression of E. coli pMTL1015 clones following growth in Hy-soy-based semi-defined medium.

| Clone Name | | E. coli host | Sample time (h) | *Gel estimate | rPA (μg/mL culture) ELISA |
|---|---|---|---|---|---|
| 5 | pMTL1015-pelB-PA-wt | RV308 | 16 | <100 | 50 |
| 6 | pMTL1015-ompA-PA-wt | RV308 | 16 | <100 | 64 |
| 7 | pMTL1015-cpg-PA-wt | RV308 | 16 | <100 | 56 |
| 8 | pMTL1015-pelB-PA-synt | RV308 | 20 | >100 | 224 |
| 9 | pMTL1015-cpg-PA-synt | RV308 | 20 | >100 | 170 |
| 10 | pMTL1015-ompA-PA-synt | RV308 | 20 | >100 | 189 |

*estimate of rPA concentration from SDS-PAGE by comparison with 100 μg/mL rPA standard Example 3

Fermenter Level Comparisons of rPA Expression

Evaluation of the following four down-selected clones in fermenter culture was continued:

E. coli RV308 pMTL1015-cpg-PA-synt

E. coli RV308 pMTL1015-ompA-PA-synt

E. coli RV308 pMTL1015-ompA-PA-wt

E. coli DH5 pTrcK-pelB-PA-synt

Medium Selection

8 L fermentations were performed in each medium under conditions as previously described with DOT and pH control.

The growth curves obtained were similar to those seen previously with the same media (see FIG. 10), but the rPA yield from production medium (Run No: PRECRV0034: Table 4) was 2500 μg/mL by ELISA. This culture was fed with 80 mL of 50% glucose solution prior to glucose depletion in the culture. A growth curve for PRECRV0034 showing rPA production can be seen in FIG. 11, but data does not indicate whether the yield has reached a maximum when the culture was harvested.

In order to determine whether the improved rPA yields obtained for E. coli RV308 pMTL1015-cpg-PA-synt when cultured in production also occurred in the other two down-selected pMTL1015 clones, parallel fermentations were set up for all three strains under these conditions. However, the 80 mL of 50% glucose fed to the previous cultures was included from the start, raising the initial glucose concentration to 25 g/L.

E. coli RV308 pMTL1015-cpg-PA-synt again gave a yield of 2500 μg/mL and E. coli RV308 pMTL1015-ompA-PA-synt yielded 2000 μg/mL (see PRECRV0038 and 0037, Table 4).

E. coli DH5α pTrcK-pelB-PA-synt was grown in PPTB-gly at 8 L scale (see Table 4, PRECDH0013) with the exception that the OD$_{660}$ at induction was raised to 15. The rPA yield was not improved significantly over previous results although more biomass was produced with a higher final OD$_{600}$ of 26 at four hours post induction with IPTG.

Effect of Growth Temperature

Previous development programs incorporating the *E. coli* RV308 pMTL1015-cpg-host/vector system have indicated that expression of product is most efficient at temperatures between 25 and 30° C.

Assessment of the effect on yield and product stability of growth at lower temperatures of *E. coli* RV308 pMTL1015-cpg-PA-synt was made by culturing the strain in production medium, under conditions described above, at 30, 28 and 25° C. (see Table 4, PRECRV0039, 0040 and 0041 respectively).

The yields from production at the lower temperatures were lower than when grown at 30° C. The quality of the material produced did not improve with the reduction in temperature, with little or no reduction in minor impurity bands on SDS-PAGE/Western Blot.

Effect of Antibiotic Concentration

As a confirmation of the stability of the plasmid under reduced antibiotic selective pressure, *E. coli* RV308 pMTL1015-cpg-PA-synt was cultured in production medium, under conditions described above, with varying tetracycline concentration levels in the medium (see Table 4, PRECRV0042-0044). The tetracycline concentrations were 15 µg/mL (100%), 1.5 µg/mL (10%) and 0. The 2° seed cultures contained 15, 1.5 and 15 µg/mL respectively. Thus the fermenter with no added antibiotic relied on carryover from the secondary seed to supply any selective pressure, assuming no degradation of the tetracycline during the seed growth. The volume of seed transferred to the fermenter was 124 mL giving a nominal 0.23 µg/mL tetracycline in the fermentation medium at inoculation.

The yields in terms of final $OD_{600}$ and biomass were within the expected range, but the yield of rPA was slightly lower than expected for the 15 µg/mL control. The levels for the reduced antibiotic cultures were slightly higher. The stability of the pMTL1015-cpg-PA-synt plasmid was confirmed by tooth-picking final fermentation sample colony isolates onto selective (L-agar with 15 µg/mL tetracycline) and non-selective media. The results of 100, 98 and 96% growth on selective medium for 15, 1.5 and 0 µg/mL tetracycline fermentations respectively, indicate good stability under the conditions used. The viable count results for PPTBgluc2.5xYE fermentations are in the $2 \times 10^{10}$-$5 \times 10^{10}$ cfu/mL range.

TABLE 4

Summary Table of fermentations.

| Run no. | Clone | Medium (No.) | Seed $OD_{600}$ | Fermenter $OD_{600}$ | SDS-PAGE (mg/L) | ELISA (mg/L) |
|---|---|---|---|---|---|---|
| PRECRV0031 | pMTL1015-cpg-PA-synt | PPTBgluc | 12.6 | 34.8 | 100+ | 320 |
| PRECRV0032 | pMTL1015-cpg-PA-synt | PPTBgluc YEx1.5 | 13.0 | 44.2* | 100* | 84* |
| PRECRV0033 | pMTL1015-cpg-PA-synt | PPTBgluc YEx2 | 14.7 | 59.8 | 500++ | 1630 |
| PRECRV0034 | pMTL1015-cpg-PA-synt | PPTBgluc YEx2.5 | 14.2 | 71.6 | 500++ | 2500 |
| PRECDH0013 | pTrcK-pelB-PA-synt | PPTBgly | 2.67 | 26.2 | 100++ | 360-465 |
| PRECRV0036 | pMTL1015-ompA-PA-wt | PPTBgluc YEx2.5 | 14.8 | 43.9* | <100* | 90* |
| PRECRV0037 | pMTL1015-ompA-PA-synt | PPTBgluc YEx2.5 | 8.7 | 56.6 | 500++ | 2000 |
| PRECRV0038 | pMTL1015-cpg-PA-synt | PPTBgluc YEx2.5 | 14.7 | 62.6 | 500++ | 2500 |
| PRECRV0039 | pMTL1015-cpg-PA-synt | PPTBgluc YEx2.5 | 15.6 | 62.4 | 500++ | 2300 |
| PRECRV0040 | pMTL1015-cpg-PA-synt | PPTBgluc YEx2.5 | 15.6 | 62.2 | 500++ | 1600 |
| PRECRV0041 | pMTL1015-cpg-PA-synt | PPTBgluc YEx2.5 | 15.6 | 63.6 | 500++ | 1500 |
| PRECRV0042 | pMTL1015-cpg-PA-synt | PPTBgluc YEx2.5 | 12.9 | 62.4 | 500++ | 1720 |
| PRECRV0043 | pMTL1015-cpg-PA-synt | PPTBgluc YEx2.5 | 13.2 | 66.4 | 500++ | 1800 |
| PRECRV0044 | pMTL1015-cpg-PA-synt | PPTBgluc YEx2.5 | 12.9 | 63.8 | 500++ | 2120 |

PPTB—Phytone Peptone-based Terrific Broth; gluc—glucose; YE—Yeast Extract

Selection of Production Strain

The results obtained to date for the clones investigated after the initial down-selection have shown that of the four, *E. coli* RV308 pMTL1015-cpg-PA-synt has, in most cases, shown the highest yield when compared with the other pMTL1015 clones under equivalent conditions.

The largest proportion of information generated has been from the *E. coli* RV308 pMT1015-cpg-PA-synt clone, for both fermentation and DSP development and with yields in the 1.5-2.5 mg/mL range when production medium has been used. This has allowed the present applicant to select this clone as their preferred production organism for all future work.

Table 5 shows a summary of all cultures grown to date in production medium. The figures indicate that although 2500 µg/mL is achievable, a more realistic value for the yield is 2000 µg/mL.

TABLE 5

Comparison of rPA levels relative to cell wet weight and optical density at harvest for cultures of E. coli RV308 pMTL1015-cpg-PA-synt containing 2.5x yeast extract.

| Run No. | Culture $OD_{600}$ | Cell Weight (g/L) | rPA Yield (mg/L) | mg rPA/ OD unit | mg rPA/g wet weight |
|---|---|---|---|---|---|
| PRECRV0030 | 69.8 | 85.8 | 1900 | 27.2 | 22.1 |
| PRECRV0034 | 71.6 | 102 | 2500 | 34.9 | 24.5 |
| PRECRV0038 | 62.6 | 86.5 | 2500 | 39.9 | 28.9 |
| PRECRV0039 | 62.4 | 77.5 | 2300 | 36.9 | 29.7 |
| PRECRV0040 | 62.2 | 80.4 | 1600 | 25.7 | 19.9 |
| PRECRV0041 | 63.6 | 98.5 | 1500 | 23.5 | 15.2 |
| PRECRVO042 | 62.4 | 89.1 | 1720 | 27.6 | 19.3 |
| PRECRV0043 | 66.4 | 88.8 | 1800 | 27.1 | 20.3 |
| PRECRV0044 | 63.8 | 83.9 | 2120 | 33.2 | 25.3 |
| MEAN | 65.0 | 88.1 | 1993 | 30.7 | 22.8 |

Example 4

Upstream Process for rPA Production

Seed Banks for Clone of Interest—Clone pMTL1015-cpg-PA-synt transformed into E. coli RV308 (ATCC 31608).

After sequence confirmation, a research seed bank was prepared by growth under selective pressure of tetracycline (15 mg/L) in soy peptone based L-broth (Phytone peptone 15 g/L, Bacto yeast extract 5 g/L, NaCl 5 g/L, pH 6.8-7.0). A single colony from a nutrient agar plate with tetracycline was inoculated into 100 mL medium in 500 mL baffled shake flasks and incubated at 30° C. and 150 rpm in a shaking incubator until $OD_{600}$ reached 1.5. The culture was then mixed with sterile 50% glycerol in growth medium (see above) to give a final glycerol concentration of 10%, and stored frozen at −80° C. as 1 mL aliquots in 1.8 mL cryovials.

A working research cell bank (WRCB) of 250 vials was prepared from above seed bank using the same conditions and medium for growth, however 250 µL of thawed vial contents were inoculated into 200 mL medium in 1000 mL baffled shake flasks.

Primary Seed Culture 1 vial of WRCB was thawed and 100 µL inoculated into 10 mL soy peptone based L-Broth (see above) containing tetracycline at 15 mg/L in a 25 mL universal bottle, incubated at 30° C. with shaking at 150 rpm for 7-9 hours. This was a recovery step to ensure that the organism is viable and to give a more consistent seed production process. The final $OD_{600}$ of this step was 0.7-1.0.

Secondary Seed Culture

This step produces the inoculum for the fermentation, and with a reasonably sized shaking incubator is capable of producing inocula sufficient for 5-250 L cultures in shake flasks. At 50 L scale, 200 µL of primary seed was inoculated into 200 mL of production medium in each of 5×1000 mL baffled shake flasks. The cultures were incubated with shaking at 150 rpm and 30° C. for 11-12 hours giving a final $OD_{600}$ of 13-16.

To prevent precipitation and caramelisation of some components during sterilisation by autoclaving, production medium is prepared by sterilising the complex component as a bulk and then adding the glucose, phosphate, magnesium and tetracycline aseptically as sterile solutions when the temperature of the components has fallen to lower than 25° C.

Production Fermentation

The seed cultures were then bulked and a volume sufficient to give a starting $OD_{600}$ of 0.2 in the fermenter was inoculated into 50 L production medium (see above) in a 72 L APPLIKON stirred tank fermenter. The complex medium components were sterilised, as a 40 L bulk, in situ at 121-123° C. for 30 minutes, cooled to below 25° C. and then supplemented with the remaining components to bring the total volume to 50 L.

The culture was then grown as a batch at a temperature of 30(±0.5)° C., pH 7.0 controlled by addition of sodium hydroxide and phosphoric acid. Dissolved oxygen tension was maintained at >40% by cascade step control of the following parameters: agitation (200-800 rpm), backpressure (3-7 psi), sparged airflow (25-50 Lpm) and oxygen supplementation (0-20 Lpm), in the order described.

When growth had ceased (12-14 hours), as measured by OD ($OD_{600}$ 60-65), the culture was chilled to below 15° C. and harvested by batch centrifugation (SORVALL RC-3B centrifuge, H6000A rotor, 5000 rpm for 15 minutes). The harvested cell paste was stored at −20° C. until required for downstream processing. Product expression was assessed by ELISA assay from samples removed hourly from the culture.

Example 5

Downstream Processing Steps

Cell Breakage

Approximately 4.5 kg of frozen cell paste harvest were suspended into a smooth paste with, initially, a minimum volume of 20 mM TRIS/1 mM EDTA pH 8.5. Further buffer was added to give an overall suspended volume of 16 L.

The suspended cells were broken by passing twice through an 'APV Gaulin' high-pressure homogeniser at a pressure of 7000 psi. The homogenate was then centrifuged for 1 hour at 5000 rpm in a 'Sorval' RC3 centrifuge. The pellet was discarded, and the supernatant (16 L approx) was retained.

Diafiltration

The centrifuged homogenate was diafiltered with 3 times its volume of purified water using a MILLIPORE PELLICON membranous filtering unit concentrator fitted with two PALL OS030F07 0.5 $m^2$ 'Centrasette 2 Omega' suspended screen channel 30 kDa membranes. The concentrator was operated at a flow rate of 17 L/min with a trans-membrane pressure of 1.6 Bar. The pH was adjusted to 8.0 and the conductivity to 2 mS/cm.

Anion Exchange and Chromatography

A 25 cm diameter chromatography column was packed with 5 L of AMERSHAM Q-SEPHAROSE FAST FLOW separation media anion exchanger to give a bed height of 10 cm. An industrial UV monitor was then connected to the effluent line. The column was operated at a flow-rate of 330 mL/min throughout. The packed column was washed with 10 L of water, then 5 L of 0.5 M sodium hydroxide, followed by purified water. 10 L of 0.5 M TRIS, pH 8.0, was pumped, and the column was then equilibrated with start buffer (20 mM TRIS, pH 8.0).

The diafiltrate was loaded, and then the loaded column was washed to baseline resolution with start buffer. The bound rPA was eluted with increasing salt steps of 10, 20, and 65 mM sodium chloride in start buffer, and the eluted peaks were collected in separate appropriately sized vessels. The eluates were assayed by SDS-PAGE and SEC-HPLC, and the fractions containing rPA at a purity of >40% were retained.

The column was regenerated by passing sequentially 10 L of 2 M sodium chloride, followed by 10 L of 1 M sodium acetate, 10 L of 0.5 M sodium hydroxide, then 10 L of 50 mM sodium hydroxide for storage.

Hydrophobic Charge Induction Chromatography

A 30 cm diameter column connected to UV monitor was packed with 20 L of CIPHERGEN MEP HYPERCEL chromatographic sorbent at a flow rate of 7 L/min. Once packed, all further steps were performed at 800 mL/min. The column was washed with 5 L of 1 M sodium hydroxide with a contact time of no more than 40 min. The column was then washed with water, and then equilibrated with 20 L loading buffer (50 mM TRIS, pH 8.0). The Q pool (i.e. the pool from the previous Q chromatography step) was loaded, the column was washed with loading buffer to baseline, then the bound rPA was eluted with purified water. The collected product was assayed by SDS-PAGE and SEC-HPLC. The MEP pool (i.e. the pool from the MEP HYPERCEL chromatographic sorbent column) was filtered through a 0.22 μm, 2000 cm$^2$ PALL POSIDYNE membrane filter. The column was regenerated with 10 L of 1 M sodium hydroxide, washed with purified water, and then stored in 0.2 μm filtered 50 mM sodium hydroxide.

Diafiltration and Formulation

The purified rPA was diafiltered using a 'PALL Centramate' medium screen OMEGA 50 kDa cartridge (part No. OS0350C12, 0.093 m$^2$). A flow-rate of 800 mL/min, and a transmembrane pressure of 1.6 Bar were used. The diafiltration was performed versus 5 L of formulation buffer; 25 mM sodium phosphate, 150 mM sodium chloride, pH 8.0. A further filtration was performed using a 0.22 μm PALL POSIDYNE membrane filter of 5000 cm$^2$ area, and then the final product was dispensed into appropriate vials.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

The teachings of each of the following references are hereby incorporated by reference in their entirety:

Abrahmsen (1986). Nucl. Acids Res. 14: 7487-7500
Alldread et al. (1992). Gene 14: 139-143
Altschul (1990) J. Mol. Biol. 215: pgs. 403-410
Ausubel F. M. et al., Current Protocols in Molecular Biology, eds, Current Protocols, a joint venture between Greene Publishing Associates, In. And John Wiley & Sons, Inc. (1995 Supplement) Ausubel
Baillie, L. (2001), 91, pgs 609-613
Batra, S. (2001) Biochem. and Biophys. Res. Comm., 281, pgs 186-192
Better et al. (1988) Science 240:1041-1043
Bhatnagas, R. (2001) Critical Rev. in Microbiol., 27(3), 167-200
Bolivar et al. (1977) Gene 2: 95
Brehm et al. (1991) Appl. Microbiol Biotechnol 36: 358-363
Brosius et al. (1981) J Mol Biol 148: 107-127
Chambers et al. (1988) Gene 68: 139-149
Chambers et al. (1992) FEMS Microbiol Letters 91: 277-284
Denefle et al. (1989) Gene 85: 499-510
Fujimoto et al. (1988) J. Biotechnol. 8: 77-86
Ghrayeb et al. (1984) EMBO J. 3: 2437-2442
Gray et al. (1985) Gene 39: 247-254
Hoffman & Wright (1985) Proc. Nat. Acad. Sci. USA. 82: 5107-5111
Johnson et al. (1996) Protein Expression Purif. 7: 104-1123
Kadonaga et al. (1984) J Biol Chem. 259: 2149-2154
Kanehisa (1984) Nuc. Acids Res. 12:203-213
Le Calvez et al. (1996) Gene 170: 51-55
Lei et al. (1987) J. Bacteriol. 169: 4379-4383
Little, S. F. (1986) Inf. and Immunol. vol. 52, No. 2, 509-512
Macyntyre & Henning (1990). Biochimmie 72: 157-167
Makrides (1996) Microbiological Reviews 60: 512-538
Maniatis et al. (1991) Molecular Cloning: A laboratory Manual. Cold Spring Harbor, N.Y., Cold Spring Harbor Laboratory Press
Michael et al. (1994) FEMS Microbiol. Letters 124: 195-202
Miller et al. (1983) Gene 24: 309-315
Minton et al. (1988) Focus 10: 56
Morioka-Fujimoto et al. (1991) J. Biol. Chem. 266: 1728-1732
Needleman & Wunsch (1970) J. Mol. Biol. 48: 443
Oka et al. (1985) Proc. Nat. Acad. Sci. USA. 82: 7212-7216
Pearson & Lipman (1988) Proc. Nat. Acad. Sci. USA 85: 2444
Price, B. M. (2001) Inf. and Immun., vol. 69, No. 7, 4509-4515
Proudfoot et al. (1996) J. Biol. Chem. 271: 2599-2603
Sambrook et al. (1989) Molecular Cloning: A laboratory Manual. Second Edition. Cold Spring Harbor Laboratory Press
Sambrook and Russell (2001) Molecular Cloning: A laboratory Manual. Third Edition. Cold Spring Harbor Laboratory Press
Schein et al. (1992) Biochem. J. 283: 137-144
Sharma et al. (1996) Protein Expression and Purification. 7, 33-38
Smith and Waterman (1981) Adv. Appl. Math. 2: 484
Sterne, M. (1939) Onderstepoort J. of Veterinary Science and Animal Industry, 13, 307-312
Tucker et al. (1983) Gene 24: 309-15
Villa-Komaroff et al. (1977) Proc. Nat. Acad. Sci. USA. 75: 3727-3731
Vodkin, M. et al. (1983) Cell, 34:693
Watson, (1984) Proc. Nat. Acad. Sci. USA. vol. 12: 5145
Welkos, S., et al. (1988) Gene, 69(2): 287
Wetmur and Davidson (1968) J. Mol. Biol. 31:349-370

What is claimed is:

1. An isolated polynucleotide comprising the nucleic acid sequence of SEQ ID NO:1, wherein said polynucleotide encodes a recombinant *Bacillus anthracis* Protective Antigen (rPA).

2. An isolated polynucleotide according to claim 1, further comprising a polynucleotide encoding a carboxypeptidase $G_1$ or carboxypeptidase $G_2$ secretion sequence.

3. An isolated polynucleotide according to claim 1, further comprising a polynucleotide encoding a secretion sequence for periplasmic translocation of said recombinant *Bacillus anthracis* Protective Antigen (rPA).

4. An isolated polynucleotide according to claim 1, further comprising a polynucleotide encoding a secretion sequence for extracellular translocation of said recombinant *Bacillus anthracis* Protective Antigen (rPA).

5. An isolated polynucleotide according to claim 3, wherein said secretion sequence is cleavable from said recombinant *Bacillus anthracis* Protective Antigen (rPA) during periplasmic translocation.

6. An isolated polynucleotide according to claim 4, wherein said secretion sequence is cleavable from said recombinant *Bacillus anthracis* Protective Antigen (rPA) during extracellular translocation.

7. An isolated polynucleotide according to claim 2, wherein the carboxypeptidase $G_2$ secretion sequence is encoded by the nucleic acid sequence of SEQ ID NO:3.

8. An isolated polynucleotide according to claim 1, which further comprises a codon encoding a methionine residue at the 5' end.

9. An isolated polynucleotide according to claim 8, wherein said polynucleotide comprises the nucleic acid sequence of SEQ ID NO:7.

10. An expression vector comprising the polynucleotide of claim 1.

11. An expression vector according to claim 10, further comprising a promoter that is selected so as to ensure that the rPA polypeptide is highly expressed.

12. An expression vector according to claim 11, wherein said promoter is a malate dehydrogenase (mdh) promoter.

13. An expression vector according to claim 10 further comprising a selectable marker.

14. An expression vector according to claim 10, wherein said vector expresses the polynucleotide in the absence of a chemical inducer.

15. An expression vector according to claim 11, wherein the vector is the plasmid pMTL1015, comprising the nucleic acid sequence of SEQ ID NO:4.

16. An expression vector according to claim 11, wherein the vector is deposited with the ECACC under the accession number 04061401.

17. An isolated host cell grown in vitro, comprising the expression vector according to claim 10.

18. An isolated host cell according to claim 17, wherein said host is an *E. coli* cell.

19. An isolated host cell according to claim 18, wherein said *E. coli* cell is *E. coli* RV308.

20. A kit comprising one or more of: a polynucleotide according to claim 1; an expression vector according to claim 10; and an isolated host cell according to claim 17.

21. A vector comprising the nucleic acid sequence of SEQ ID NO:4.

22. The vector deposited with the ECACC under the accession number 04061401.

23. The vector deposited with the ECACC under the accession number 04052501.

* * * * *

SEQUENCE LISTING

<160> NUMBER OF SEQ ID NOS: 9

<210> SEQ ID NO 1
<211> LENGTH: 2208
<212> TYPE: DNA
<213> ORGANISM: Artificial Sequence
<220> FEATURE:
<223> OTHER INFORMATION: Description of Artificial Sequence: Synthetic rPA sequence

<400> SEQUENCE: 1

```
gaagtgaaac aggagaaccg tctgctgaac gaaagcgaat ctagctctca gggcctgctg      60
ggctactatt tcagcgatct gaactttcag gcaccgatgg ttgtgacctc tagcacgacc     120
ggcgatctga gcattccgag cagcgaactg gagaacattc cgagcgagaa ccagtacttt     180
cagtctgcga tttggagcgg cttcatcaaa gtgaagaaaa gcgatgagta ccctttgcg      240 acgtctgcgg ataaccatgt gaccatgtgg gtggacgatc aggaagtgat caacaaagcg     300
agcaacagca acaagattcg cctggagaag ggtcgcctgt atcagatcaa gattcagtat     360
cagcgcgaga atccgaccga gaaaggcctg gatttcaaac tgtactggac cgatagccag     420
aacaagaaag aagtgattag ctctgataac ctgcaactgc cggaactgaa acagaagagc     480
agcaacagcc gcaagaaacg cagcacctct gcaggcccga ccgttccaga tcgcgacaac     540
gatggcattc cggacagcct ggaagtggaa ggttataccg ttgatgtgaa gaacaaacgc     600
accttcctga gcccgtggat tagcaacatt catgagaaga aaggcctgac caagtacaaa     660
agcagcccgg agaagtggag caccgcgagc gatccgtata gcgactttga gaaagtgacc     720
ggccgcattg ataagaacgt gagcccggaa gcgcgtcacc cactggttgc agcgtatccg     780
attgtgcatg ttgacatgga aacatcatt ctgagcaaga acgaagatca gagcacccag     840
aacacggata gccagacccg cacgatcagc aagaacacca gcacgagccg tacccatacc     900
agcgaagtgc atggcaatgc ggaagtgcat gcgagcttct ttgacattgg tggcagcgtg     960
agcgcgggct tcagcaacag caacagcagc accgtggcga ttgatcatag cctgagcctg    1020
gcgggcgaac gtacctgggc ggaaaccatg ggcctgaaca cggcggatac ggcacgtctg    1080
aatgcgaaca ttcgctatgt gaacaccggt accgcgccaa tctataacgt tctgccgacc    1140
acgagcctgg tgctgggcaa gaatcagacc ctggcgacca tcaaagcgaa agagaaccag    1200
ctgtctcaga ttctggcacc gaacaactac tatccgagca gaacctggc accgattgca     1260 ctgaatgcgc aggatgactt cagcagcacc ccgatcacca tgaactacaa tcagtttctg    1320
gagctggaga gaccaaaaca actgcgcctg gataccgatc aggtgtatgg caacattgcg    1380
acctacaact ttgagaacgg ccgcgttcgc gtggataccg gtagcaactg gtctgaagtg    1440
ctgccgcaga ttcaggaaac gaccgcgcgc atcatcttca cggcaaaaga tctgaacctg    1500
gtggaacgtc gcatcgcggc agtgaaccca tctgatccac tggaaacgac caaaccggac    1560
atgaccctga aagaagcgct gaagattgca tttggcttca cgaaccgaa tggcaacctg     1620 cagtatcagg gcaaagacat caccgagttt gacttcaact ttgatcaaca gacctctcag    1680
aacatcaaga accagctggc agaactgaat gcgaccaaca tctacaccgt gctggacaag    1740
atcaaactga acgcaaagat gaacattctg attcgtgaca aacgcttcca ctatgatcgt    1800
aacaacattg cggtgggtgc agatgaaagc gttgtgaaag aagcgcatcg tgaagtgatc    1860
aactctagca ccgaaggcct gctgctgaac attgacaaag acatccgtaa gattctgagc    1920
```

-continued

| | |
|---|---|
| ggctacattg tggagattga agataccgaa ggtctgaaag aagtgatcaa cgatcgctat | 1980 |
| gacatgctga acatctctag cctgcgccag gatggcaaga ccttcattga cttcaagaag | 2040 |
| tacaacgaca aactgccgct gtacatcagc aatccgaact acaaagtgaa cgtgtatgcg | 2100 |
| gtgaccaaag agaacaccat cattaaccca agcgagaatg gcgataccag caccaacggc | 2160 |
| atcaagaaga ttctgatctt cagcaagaaa ggctatgaga ttggctaa | 2208 |

<210> SEQ ID NO 2
<211> LENGTH: 2208
<212> TYPE: DNA
<213> ORGANISM: Bacillus anthracis

<400> SEQUENCE: 2

| | |
|---|---|
| gaagttaaac aggagaaccg gttattaaat gaatcagaat caagttccca ggggttacta | 60 |
| ggatactatt ttagtgattt gaattttcaa gcacccatgg tggttacctc ttctactaca | 120 |
| ggggatttat ctattcctag ttctgagtta gaaaatattc catcggaaaa ccaatatttt | 180 |
| caatctgcta tttggtcagg atttatcaaa gttaagaaga gtgatgaata cattttgct | 240 |
| acttccgctg ataatcatgt aacaatgtgg gtagatgacc aagaagtgat taataaagct | 300 |
| tctaattcta acaaaatcag attagaaaaa ggaagattat atcaaataaa aattcaatat | 360 |
| caacgagaaa atcctactga aaaggattg gatttcaagt tgtactggac cgattctcaa | 420 |
| aataaaaaag aagtgatttc tagtgataac ttacaattgc cagaattaaa acaaaaatct | 480 |
| tcgaactcaa gaaaaaagcg aagtacaagt gctggaccta cggttccaga ccgtgacaat | 540 |
| gatggaatcc ctgattcatt agaggtagaa ggatatacgg ttgatgtcaa aataaaaga | 600 |
| acttttcttt caccatggat ttctaatatt catgaaaaga aaggattaac caaatataaa | 660 |
| tcatctcctg aaaaatggag cacggcttct gatccgtaca gtgatttcga aaaggttaca | 720 |
| ggacggattg ataagaatgt atcaccagag gcaagacacc cccttgtggc agcttatccg | 780 |
| attgtacatg tagatatgga gaatattatt ctctcaaaaa atgaggatca atccacacag | 840 |
| aatactgata gtcaaacgag aacaataagt aaaaatactt ctacaagtag gacacatact | 900 |
| agtgaagtac atggaaatgc agaagtgcat gcgtcgttct ttgatattgg tgggagtgta | 960 |
| tctgcaggat ttagtaattc gaattcaagt acggtcgcaa ttgatcattc actatctcta | 1020 |
| gcagggaaa gaacttgggc tgaaacaatg ggtttaaata ccgctgatac agcaagatta | 1080 |
| aatgccaata ttgatatgt aaatactggg acggctccaa tctacaacgt gttaccaacg | 1140 |
| acttcgttag tgttaggaaa aaatcaaaca ctcgcgacaa ttaaagctaa ggaaaaccaa | 1200 |
| ttaagtcaaa tacttgcacc taataattat tatccttcta aaaacttggc gccaatcgca | 1260 |
| ttaaatgcac aagacgattt cagttctact ccaattacaa tgaattacaa tcaatttctt | 1320 |
| gagttagaaa aaacgaaaca attaagatta gatacggatc aagtatatgg aatatagca | 1380 |
| acatacaatt tgaaaatgg aagagtgagg gtggatacag gctcgaactg gagtgaagtg | 1440 |
| ttaccgcaaa ttcaagaaac aactgcacgt atcatttta atggaaaaga tttaaatctg | 1500 |
| gtagaaaggc ggatagcggc ggttaatcct agtgatccat tagaaacgac taaaccggat | 1560 |
| atgacattaa agaagcccct taaaatagca tttggattta acgaaccgaa tggaaactta | 1620 |
| caatatcaag ggaagacat aaccgaattt gatttaatt tcgatcaaca acatctcaa | 1680 |
| aatatcaaga atcagttagc ggaattaaac gcaactaaca tatatactgt attagataaa | 1740 |
| atcaaattaa atgcaaaaat gaatatttta ataagagata aacgttttca ttatgataga | 1800 |
| aataacatag cagttggggc ggatgagtca gtagttaagg aggctcatag agaagtaatt | 1860 |

-continued

| | |
|---|---|
| aattcgtcaa cagagggatt attgttaaat attgataagg atataagaaa aatattatca | 1920 |
| ggttatattg tagaaattga agatactgaa gggcttaaag aagttataaa tgacagatat | 1980 |
| gatatgttga atatttctag tttacggcaa gatggaaaaa catttataga ttttaaaaaa | 2040 |
| tataatgata aattaccgtt atatataagt aatcccaatt ataaggtaaa tgtatatgct | 2100 |
| gttactaaag aaaacactat tattaatcct agtgagaatg gggatactag taccaacggg | 2160 |
| atcaagaaaa ttttaatctt ttctaaaaaa ggctatgaga taggataa | 2208 |

<210> SEQ ID NO 3
<211> LENGTH: 78
<212> TYPE: DNA
<213> ORGANISM: Artificial Sequence
<220> FEATURE:
<223> OTHER INFORMATION: Description of Artificial Sequence: Synthetic polynucleotide encoding cpg secretion sequence

<400> SEQUENCE: 3

| | |
|---|---|
| catatgcgcc catccatcca ccgcacagcc atcgccgccg tgctggctac cgccttcgtg | 60 |
| gcgggcaccg ccctggcc | 78 |

<210> SEQ ID NO 4
<211> LENGTH: 3527
<212> TYPE: DNA
<213> ORGANISM: Artificial Sequence
<220> FEATURE:
<223> OTHER INFORMATION: Description of Artificial Sequence: Synthetic plasmid sequence pMTL1015

<400> SEQUENCE: 4

| | |
|---|---|
| cagtaagacg ggtaagcctg ttgatgatac cgctgcctta ctgggtgcat tagccagtct | 60 |
| gaatgacctg tcacgggata tcccgaagtg gtcagactgg aaaatcagag ggcaggaact | 120 |
| gctgaacagc aaaaagtcag atagcaccac atagcagacc cgccataaaa cgccctgaga | 180 |
| agcccgtgac gggctttttct tgtattatgg gtagtttcct tgcatgaatc cataaaaggc | 240 |
| gcccaatacg caaaccgcct ctccccgcgc gttggagctt gcatgcaaat tctgcttaaa | 300 |
| agtaaattaa ttgttatcaa attgatgttg ttttggctga acggtagggt atattgtcac | 360 |
| cacctgttgg aatgttgcgc taatgcataa gcgactgtta attacgtaag ttaggttcct | 420 |
| gattacggca attaaatgca taaacgctaa acttgcgtga ctacacattc ttgagatgtg | 480 |
| gtcattgtaa acggcaattt tgtggattaa ggtcgcggca gcggagcaac atatcttagt | 540 |
| ttatcaatat aataaggagt ttcatatgac catgattacg aattcgagct cggtacccgg | 600 |
| ggatcctcta gagtcgacgt cacgcgtcca tggagatctc gaggcctgca ggcatgcaag | 660 |
| cttggcactg gccgtcgttt tacaacgtcg tgactgggaa accctggcg ttacccaact | 720 |
| taatcgcctt gcagcacatc ccccttttcgc gagctggcgt aatagcgaag aggcccgcac | 780 |
| cgatcgccct tcccaacagt tgcgcagcct gaatggcgaa tggcgccgat ggtagtgtgg | 840 |
| ggtctcccca tgcgagagta gggaactgcc aggcatcaaa taaaacgaaa ggctcagtcg | 900 |
| aaagactggg cctttcgttt tatctgttgt ttgtcggtga acgctctcct gagtaggaca | 960 |
| aatccgccgg gagcggattt gaacgttgcg aagcaacggc ccggagggtg cgggcagga | 1020 |
| cgcccgccat aaactgccag gcatcaaatt aagcagaagg ccatcctgac ggatggcctt | 1080 |
| tttgcgtttc tacaaactct tttgtttatt tttctaaata cattcaaata tgtatccgct | 1140 |
| catgagacaa taaccctgat aaatgcttca ataatgatct gttaattcga gctcgcccaa | 1200 |

```
ttctcatgtt tgacagctta tcatcgaata gctttaatgc ggtagtttat cacagttaaa    1260
ttgctaacgc agtcaggcac cgtgtatgaa atctaacaat gcgctcatcg tcatcctcgg    1320
caccgtcacc ctggatgctg taggcatagg cttggttatg ccggtactgc cgggcctctt    1380
gcgggacatc gtccattccg acagcatcgc cagtcactat ggcgtgctgc tagcgctata    1440
tgcgttgatg caatttctat gcgcacccgt tctcggagca ctgtccgacc gctttggccg    1500
ccgcccagtc ctgctcgctt cgctacttgg agccactatc gactacgcga tcatggcgac    1560
cacacccgtc ctgtggattc tctacgccgg acgcatcgtg gccggcatca ccggcgccac    1620
aggtgcggtt gctggcgcct atatcgccga catcaccgat ggggaagatc gggctcgcca    1680
cttcgggctc atgagcgctt gtttcggcgt gggtatggtg gcaggccccg tggccggggg    1740
actgttgggc gccatctcct tgcacgcacc attccttgcg gcggcggtgc tcaacggcct    1800
caacctacta ctgggctgct tcctaatgca ggagtcgcat aagggagagc gtcgtccgat    1860
gcccttgaga gccttcaacc cagtcagctc cttccggtgg gcgcggggca tgactatcgt    1920
cgccgcactt atgactgtct tctttatcat gcaactcgta ggacaggtgc cggcagcgct    1980
ctgggtcatt tcggcgagg accgctttcg ctggagcgcg acgatgatcg gcctgtcgct    2040
tgcggtattc ggaatcttgc acgccctcgc tcaagccttc gtcactggtc ccgccaccaa    2100
acgtttcggc gagaagcagg ccattatcgc cggcatggcg gccgacgcgc tgggctacgt    2160
cttgctggcg ttcgcgacgc gaggctggat ggccttcccc attatgattc ttctcgcttc    2220
cggcggcatc gggatgcccg cgttgcaggc catgctgtcc aggcaggtag atgacgacca    2280
tcagggacag cttcaaggat cgctcgcggc tcttaccagc ctaacttcga tcattggacc    2340
gctgatcgtc acggcgattt atgccgcctc ggcgagcaca tggaacgggt tggcatggat    2400
tgtaggcgcc gccctatacc ttgtctgcct ccccgcgttg cgtcgcggtg catggagccg    2460
ggccacctcg acctgaatgg aagcggcgg cacctcgcta acggattcac cactccaaga    2520
attggagcca atcaattctt gcggagaact gtgaatgcgc aaaccaaccc ttggcagaac    2580
atatccatcg cgtccgccat ctccagcagc cgcacgcggc gcatctcggg gggatcaact    2640
gatcaaaagg atctaggtga agatccttt tgataatctc atgaccaaaa tcccttaacg    2700
tgagttttcg ttccactgag cgtcagaccc cgtagaaaag atcaaaggat cttcttgaga    2760
tccttttttt ctgcgcgtaa tctgctgctt gcaaacaaaa aaaccaccgc taccagcggt    2820
ggtttgtttg ccggatcaag agctaccaac tctttttccg aaggtaactg gcttcagcag    2880
agcgcagata ccaaatactg ttcttctagt gtagccgtag ttaggccacc acttcaagaa    2940
ctctgtagca ccgcctacat acctcgctct gctaatcctg ttaccagtgg ctgctgccag    3000
tggcgataag tcgtgtctta ccgggttgga ctcaagacga tagttaccgg ataaggcgca    3060
gcggtcgggc tgaacggggg gttcgtgcac acagcccagc ttggagcgaa cgacctacac    3120
cgaactgaga tacctacagc gtgagctatg agaaagcgcc acgcttcccg aagggagaaa    3180
ggcggacagg tatccggtaa gcggcagggt cggaacagga gagcgcacga gggagcttcc    3240
agggggaaac gcctggtatc tttatagtcc tgtcgggttt cgccacctct gacttgagcg    3300 tcgattttg tgatgctcgt caggggggcg gagcctatgg aaaaacgcca gcaacgcggc    3360 cttttacgg ttcctggcct tttgctggcc ttttgctcac atgttctttc ctgcgttatc    3420
ccctgattct gtggataacc gtattaccgc ctttgagtga gctgataccg ctcgccgcag    3480
ccgaacgacc gagcgcagcg agtcagtgag cgaggaagcg gaagagc                  3527
```

<210> SEQ ID NO 5
<211> LENGTH: 735
<212> TYPE: PRT
<213> ORGANISM: Bacillus anthracis

<400> SEQUENCE: 5

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
    370                 375                 380

```
Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
        420                 425                 430

Thr Met Asn Tyr Asn Gln Phe Leu Glu Leu Glu Lys Thr Lys Gln Leu
    435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
        500                 505                 510

Pro Leu Glu Thr Thr Lys Pro Asp Met Thr Leu Lys Glu Ala Leu Lys
    515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
        580                 585                 590

Asp Lys Arg Phe His Tyr Asp Arg Asn Asn Ile Ala Val Gly Ala Asp
    595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
        660                 665                 670

Lys Thr Phe Ile Asp Phe Lys Lys Tyr Asn Asp Lys Leu Pro Leu Tyr
    675                 680                 685

Ile Ser Asn Pro Asn Tyr Lys Val Asn Val Tyr Ala Val Thr Lys Glu
690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
            725                 730                 735

<210> SEQ ID NO 6
<211> LENGTH: 736
<212> TYPE: PRT
<213> ORGANISM: Artificial Sequence
<220> FEATURE:
<223> OTHER INFORMATION: Description of Artificial Sequence: Synthetic
      rPA protein sequence with N-terminal methionine

<400> SEQUENCE: 6

Met Glu Val Lys Gln Glu Asn Arg Leu Leu Asn Glu Ser Glu Ser Ser
1               5                   10                  15
```

-continued

```
Ser Gln Gly Leu Leu Gly Tyr Tyr Phe Ser Asp Leu Asn Phe Gln Ala
            20                  25                  30

Pro Met Val Val Thr Ser Thr Thr Gly Asp Leu Ser Ile Pro Ser
        35                  40                  45

Ser Glu Leu Glu Asn Ile Pro Ser Glu Asn Gln Tyr Phe Gln Ser Ala
        50                  55                  60

Ile Trp Ser Gly Phe Ile Lys Val Lys Ser Asp Glu Tyr Thr Phe
 65                 70                  75                  80

Ala Thr Ser Ala Asp Asn His Val Thr Met Trp Val Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
        130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg Ser Thr Ser Ala Gly Pro Thr Val
                165                 170                 175

Pro Asp Arg Asp Asn Asp Gly Ile Pro Asp Ser Leu Glu Val Glu Gly
        180                 185                 190

Tyr Thr Val Asp Val Lys Asn Lys Arg Thr Phe Leu Ser Pro Trp Ile
        195                 200                 205

Ser Asn Ile His Glu Lys Lys Gly Leu Thr Lys Tyr Lys Ser Ser Pro
    210                 215                 220

Glu Lys Trp Ser Thr Ala Ser Asp Pro Tyr Ser Asp Phe Glu Lys Val
225                 230                 235                 240

Thr Gly Arg Ile Asp Lys Asn Val Ser Pro Glu Ala Arg His Pro Leu
            245                 250                 255

Val Ala Ala Tyr Pro Ile Val His Val Asp Met Glu Asn Ile Ile Leu
        260                 265                 270

Ser Lys Asn Glu Asp Gln Ser Thr Gln Asn Thr Asp Ser Gln Thr Arg
    275                 280                 285

Thr Ile Ser Lys Asn Thr Ser Thr Ser Arg Thr His Thr Ser Glu Val
        290                 295                 300

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
            325                 330                 335

His Ser Leu Ser Leu Ala Gly Glu Arg Thr Trp Ala Glu Thr Met Gly
        340                 345                 350

Leu Asn Thr Ala Asp Thr Ala Arg Leu Asn Ala Asn Ile Arg Tyr Val
        355                 360                 365

Asn Thr Gly Thr Ala Pro Ile Tyr Asn Val Leu Pro Thr Thr Ser Leu
    370                 375                 380

Val Leu Gly Lys Asn Gln Thr Leu Ala Thr Ile Lys Ala Lys Glu Asn
385                 390                 395                 400

Gln Leu Ser Gln Ile Leu Ala Pro Asn Asn Tyr Tyr Pro Ser Lys Asn
            405                 410                 415

Leu Ala Pro Ile Ala Leu Asn Ala Gln Asp Asp Phe Ser Ser Thr Pro
        420                 425                 430
```

```
Ile Thr Met Asn Tyr Asn Gln Phe Leu Glu Leu Glu Lys Thr Lys Gln
        435                 440                 445

Leu Arg Leu Asp Thr Asp Gln Val Tyr Gly Asn Ile Ala Thr Tyr Asn
    450                 455                 460

Phe Glu Asn Gly Arg Val Arg Val Asp Thr Gly Ser Asn Trp Ser Glu
465                 470                 475                 480

Val Leu Pro Gln Ile Gln Glu Thr Thr Ala Arg Ile Ile Phe Asn Gly
            485                 490                 495

Lys Asp Leu Asn Leu Val Glu Arg Arg Ile Ala Ala Val Asn Pro Ser
        500                 505                 510

Asp Pro Leu Glu Thr Thr Lys Pro Asp Met Thr Leu Lys Glu Ala Leu
    515                 520                 525

Lys Ile Ala Phe Gly Phe Asn Glu Pro Asn Gly Asn Leu Gln Tyr Gln
530                 535                 540

Gly Lys Asp Ile Thr Glu Phe Asp Phe Asn Phe Asp Gln Gln Thr Ser
545                 550                 555                 560

Gln Asn Ile Lys Asn Gln Leu Ala Glu Leu Asn Ala Thr Asn Ile Tyr
            565                 570                 575

Thr Val Leu Asp Lys Ile Lys Leu Asn Ala Lys Met Asn Ile Leu Ile
        580                 585                 590

Arg Asp Lys Arg Phe His Tyr Asp Arg Asn Asn Ile Ala Val Gly Ala
    595                 600                 605

Asp Glu Ser Val Val Lys Glu Ala His Arg Glu Val Ile Asn Ser Ser
610                 615                 620

Thr Glu Gly Leu Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
            645                 650                 655

Ile Asn Asp Arg Tyr Asp Met Leu Asn Ile Ser Ser Leu Arg Gln Asp
        660                 665                 670

Gly Lys Thr Phe Ile Asp Phe Lys Lys Tyr Asn Asp Lys Leu Pro Leu
    675                 680                 685

Tyr Ile Ser Asn Pro Asn Tyr Lys Val Asn Val Tyr Ala Val Thr Lys
690                 695                 700

Glu Asn Thr Ile Ile Asn Pro Ser Glu Asn Gly Asp Thr Ser Thr Asn
705                 710                 715                 720

Gly Ile Lys Lys Ile Leu Ile Phe Ser Lys Lys Gly Tyr Glu Ile Gly
            725                 730                 735

<210> SEQ ID NO 7
<211> LENGTH: 2211
<212> TYPE: DNA
<213> ORGANISM: Artificial Sequence
<220> FEATURE:
<223> OTHER INFORMATION: Description of Artificial Sequence: Synthetic
      rPA sequence with 5' methionine-encoding codon

<400> SEQUENCE: 7
atggaagtga acaggagaa ccgtctgctg aacgaaagcg aatctagctc tcagggcctg      60
ctgggctact atttcagcga tctgaacttt caggcaccga tggttgtgac ctctagcacg    120
accggcgatc tgagcattcc gagcagcgaa ctggagaaca ttccgagcga gaaccagtac    180
tttcagtctg cgatttggag cggcttcatc aaagtgaaga aaagcgatga gtataccttt    240
gcgacgtctg cggataacca tgtgaccatg tgggtggacg atcaggaagt gatcaacaaa    300
gcgagcaaca gcaacaagat tcgcctggag aagggtcgcc tgtatcagat caagattcag    360
```

-continued

```
tatcagcgcg agaatccgac cgagaaaggc ctggatttca aactgtactg gaccgatagc      420
cagaacaaga aagaagtgat tagctctgat aacctgcaac tgccggaact gaaacagaag      480
agcagcaaca gccgcaagaa acgcagcacc tctgcaggcc cgaccgttcc agatcgcgac      540
aacgatggca ttccggacag cctggaagtg aaggttata ccgttgatgt gaagaacaaa      600 cgcaccttc tgagcccgtg gattagcaac attcatgaga agaaaggcct gaccaagtac      660
aaaagcagcc cggagaagtg gagcaccgcg agcgatccgt atagcgactt tgagaaagtg      720
accggccgca ttgataagaa cgtgagcccg gaagcgcgtc acccactggt tgcagcgtat      780
ccgattgtgc atgttgacat ggagaacatc attctgagca gaacgaaga tcagagcacc      840 cagaacacgg atagccagac ccgcacgatc agcaagaaca ccagcacgag ccgtacccat      900
accagcgaag tgcatggcaa tgcggaagtg catgcgagct tctttgacat tggtggcagc      960
gtgagcgcgg gcttcagcaa cagcaacagc agcaccgtgg cgattgatca tagcctgagc     1020
ctggcgggcg aacgtacctg gcggaaacc atgggcctga acacggcgga tacggcacgt     1080
ctgaatgcga acattcgcta tgtgaacacc ggtaccgcgc caatctataa cgttctgccg     1140
accacgagcc tggtgctggg caagaatcag accctggcga ccatcaaagc gaaagagaac     1200
cagctgtctc agattctggc accgaacaac tactatccga gcaagaacct ggcaccgatt     1260
gcactgaatg cgcaggatga cttcagcagc accccgatca ccatgaacta caatcagttt     1320
ctggagctgg agaagaccaa acaactgcgc ctggataccg atcaggtgta tggcaacatt     1380
gcgacctaca actttgagaa cggccgcgtt cgcgtggata ccggtagcaa ctggtctgaa     1440
gtgctgccgc agattcagga aacgaccgcg cgcatcatct tcaacggcaa agatctgaac     1500
ctggtggaac gtcgcatcgc ggcagtgaac ccatctgatc cactgaaaac gaccaaaccg     1560
gacatgaccc tgaaagaagc gctgaagatt gcatttggct tcaacgaacc gaatggcaac     1620
ctgcagtatc agggcaaaga catcaccgag tttgacttca actttgatca acagacctct     1680
cagaacatca gaaccagct ggcagaactg aatgcgacca acatctacac cgtgctggac     1740
aagatcaaac tgaacgcaaa gatgaacatt ctgattcgtg acaaacgctt ccactatgat     1800
cgtaacaaca ttgcggtggg tgcagatgaa agcgttgtga agaagcgca tcgtgaagtg     1860 atcaactcta gcaccgaagg cctgctgctg aacattgaca aagacatccg taagattctg     1920
agcggctaca ttgtggagat tgaagatacc gaaggtctga agaagtgat caacgatcgc     1980 tatgacatgc tgaacatctc tagcctgcgc caggatggca agaccttcat tgacttcaag     2040
aagtacaacg acaaactgcc gctgtacatc agcaatccga actacaaagt gaacgtgtat     2100
gcggtgacca agagaacac catcattaac ccaagcgaga atggcgatac cagcaccaac     2160
ggcatcaaga agattctgat cttcagcaag aaaggctatg agattggcta a             2211
```

<210> SEQ ID NO 8
<211> LENGTH: 2211
<212> TYPE: DNA
<213> ORGANISM: Bacillus anthracis

<400> SEQUENCE: 8

```
atggaagtta acaggagaa ccggttatta aatgaatcag aatcaagttc ccaggggtta       60
ctaggatact attttagtga tttgaatttt caagcaccca tggtggttac ctcttctact      120 acagggatt tatctattcc tagttctgag ttagaaaata ttccatcgga aaaccaatat      180
tttcaatctg ctatttggtc aggatttatc aaagttaaga gagtgatga atatacattt      240
```

```
gctacttccg ctgataatca tgtaacaatg tgggtagatg accaagaagt gattaataaa      300
gcttctaatt ctaacaaaat cagattagaa aaaggaagat tatatcaaat aaaaattcaa      360
tatcaacgag aaaatcctac tgaaaaagga ttggatttca agttgtactg gaccgattct      420
caaaataaaa aagaagtgat ttctagtgat aacttacaat tgccagaatt aaaacaaaaa      480
tcttcgaact caagaaaaaa gcgaagtaca agtgctggac ctacggttcc agaccgtgac      540
aatgatggaa tccctgattc attagaggta gaaggatata cggttgatgt caaaaataaa      600 agaactttc tttcaccatg gatttctaat attcatgaaa agaaaggatt aaccaaatat      660
aaatcatctc ctgaaaaatg gagcacggct tctgatccgt acagtgattt cgaaaaggtt      720
acaggacgga ttgataagaa tgtatcacca gaggcaagac accccttgt ggcagcttat      780 ccgattgtac atgtagatat ggagaatatt attctctcaa aaaatgagga tcaatccaca      840
cagaatactg atagtcaaac gagaacaata agtaaaaata cttctacaag taggacacat      900
actagtgaag tacatggaaa tgcagaagtg catgcgtcgt tctttgatat tggtgggagt      960
gtatctgcag gatttagtaa ttcgaattca agtacggtcg caattgatca ttcactatct     1020
ctagcagggg aaagaacttg gctgaaaca atgggtttaa ataccgctga tacagcaaga     1080
ttaaatgcca atattagata tgtaaatact gggacggctc caatctacaa cgtgttacca     1140
acgacttcgt tagtgttagg aaaaaatcaa acactcgcga caattaaagc taaggaaaac     1200
caattaagtc aaatacttgc acctaataat tattatcctt ctaaaaactt ggcgccaatc     1260
gcattaaatg cacaagacga tttcagttct actccaatta caatgaatta caatcaatt      1320 cttgagttag aaaaaacgaa acaattaaga ttagatacgg atcaagtata tgggaatata     1380
gcaacataca attttgaaaa tggaagagtg agggtggata caggctcgaa ctggagtgaa     1440
gtgttaccgc aaattcaaga aacaactgca cgtatcattt ttaatggaaa agatttaaat     1500
ctggtagaaa ggcggatagc ggcggttaat cctagtgatc cattagaaac gactaaaccg     1560
gatatgacat aaaagaagc ccttaaaata gcatttggat ttaacgaacc gaatggaaac      1620
ttacaatatc aagggaaaga cataaccgaa tttgatttta atttcgatca acaaacatct     1680
caaaatatca agaatcagtt agcggaatta aacgcaacta acatatatac tgtattagat     1740
aaaatcaaat taaatgcaaa aatgaatatt ttaataagag ataaacgttt tcattatgat     1800
agaaataaca tagcagttgg ggcggatgag tcagtagtta aggaggctca tagagaagta     1860
attaattcgt caacagaggg attattgtta aatattgata aggatataag aaaaatatta     1920
tcaggttata ttgtagaaat tgaagatact gaagggctta agaagttat aaatgacaga      1980 tatgatatgt tgaatatttc tagtttacgg caagatggaa aaacatttat agattttaaa     2040
aaatataatg ataaattacc gttatatata agtaatccca attataaggt aaatgtatat     2100
gctgttacta agaaaaacac tattattaat cctagtgaga atgggatac tagtaccaac     2160 gggatcaaga aaattttaat cttttctaaa aaaggctatg agataggata a              2211
```

<210> SEQ ID NO 9
<211> LENGTH: 2211
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 9

```
atggaagtta aacaggagaa ccgtttgttg aatgaatgcg aatctagttc tcaggggttg       60
```

-continued

```
ctgggctact attttagtga tttgaatttt caggcaccga tggttgttac ctcttgtact      120
accggggatt tgtgtattcc tagttgtgag ttggagaata ttccgtggga gaaccagtat      180
tttcagtctg ctatttggtg cggctttatc aaagttaaga agagtgatga gtataccttt      240
gctacttctg ctgataatca tgtgaccatg tgggtggatg atcaggaagt gattaataaa      300
gcttgtaatt gtaacaagat tcgcttggag aagggtcgct tgtatcagat caagattcag      360
tatcagcgcg agaatcctac tgagaaaggc ttggatttca agttgtactg gaccgattgt      420
cagaataaga agaagtgat ttgttgtgat aacttgcaat tgccggaatt gaaacagaag      480
tgttggaact gccgcaagaa gcgcagtacc tgtgctggcc ctacggttcc agatcgtgac      540
aatgatggca ttcctgattg cttggaggtg aaggttata cggttgatgt gaagaataaa      600 cgcactttc tttgcccgtg gatttgtaat attcatgaga agaaaggctt gaccaagtat      660
aaatgctgtc ctgagaagtg gagcacggct tgtgatccgt atagtgattt tgagaaggtt      720
accggccgga ttgataagaa tgtgtgcccg gaggcgcgtc accccttgt tgcagcttat      780 ccgattgtgc atgttgatat ggagaatatt attctgtgca agaatgagga tcagtgcacc      840
cagaatactg atagtcagac gcgcacgatc agtaagaata cttgtacgag tcgtacccat      900
actagtgaag tgcatggcaa tgcggaagtg catgcgtggt tctttgatat tggtgggagt      960
gtgtgtgcgg gctttagtaa ttggaattgc agtacggtgg cgattgatca ttgcctgtgt     1020
ctggcggggg aacgtacttg ggctgaaacc atgggtttga atacggctga tacggcacgt     1080
ttgaatgcga atattcgcta tgtgaatact ggtacggctc caatctataa cgttttgccg     1140
acgacttggt tggtgttggg caagaatcag accctggcga ccattaaagc taaggagaac     1200
cagttgtgtc agattcttgc acctaataat tattatcctt gtaagaactt ggcgccgatt     1260
gcattgaatg cgcaggatga tttcagttgt actccgatta ccatgaatta caatcagttt     1320
cttgagttgg agaagacgaa acaattgcgc ttggatacgg atcaggtgta tgggaatatt     1380
gcgacctaca attttgagaa tggccgcgtt cgggtggata ccggttggaa ctggtgtgaa     1440
gtgttgccgc agattcagga aacgactgcg cgtatcattt ttaatggcaa agatttgaat     1500
ctggtggaac gtcggatcgc ggcggttaat ccttgtgatc cattggaaac gactaaaccg     1560
gatatgacct tgaaagaagc gcttaagatt gcatttggct taacgaacc gaatggcaac     1620 ttgcagtatc aggggaaaga catcaccgag tttgatttta attttgatca acagacctct     1680
cagaatatca agaatcagtt ggcggaattg aatgcgacta acatctatac tgtgttggat     1740
aagatcaaat tgaatgcaaa gatgaatatt ttgattcgtg ataaacgttt tcattatgat     1800
cgtaataaca ttgcggttgg tgcggatgag tgcgttgtta aggaggctca tcgtgaagtg     1860
attaattctt gcaccgaggg cttgttgttg aatattgata aggatatccg taagattttg     1920
tgcggttata ttgtggagat tgaagatact gaaggtctta agaagttat caatgatcgc     1980 tatgatatgt tgaatatttc tagtttgcgg caggatggca agacctttat tgattttaag     2040
aagtataatg ataaattgcc gttgtatatc agtaatccga attataaggt gaatgtgtat     2100
gctgttacta aagagaacac tattattaat cctagtgaga atggggatac tagtaccaac     2160
gggatcaaga agatttttgat cttttgtaag aaaggctatg agattggcta a               2211
```